(12) United States Patent
Wehrle-Haller et al.

(10) Patent No.: US 7,033,794 B2
(45) Date of Patent: Apr. 25, 2006

(54) BASOLATERAL SORTING SIGNAL AND INHIBITORS THEREOF

(75) Inventors: Bernhard M. Wehrle-Haller, Veyrier (CH); Beat A. Imhof, Conches (CH)

(73) Assignee: Universite de Geneve, Geneva (CH)

( * ) Notice: Subject to any disclaimer, the term of this patent is extended or adjusted under 35 U.S.C. 154(b) by 360 days.

(21) Appl. No.: 10/176,791

(22) Filed: Jun. 20, 2002

(65) Prior Publication Data

US 2003/0237101 A1 Dec. 25, 2003

Related U.S. Application Data

(63) Continuation of application No. PCT/EP00/13141, filed on Dec. 22, 2000.

(30) Foreign Application Priority Data

Dec. 23, 1999 (CH) .............................. PCT/CH99/00624

(51) Int. Cl.
*A01K 67/00* (2006.01)
*A61K 38/08* (2006.01)
*C07K 7/06* (2006.01)

(52) U.S. Cl. .................... 435/69.1; 514/16; 530/329
(58) Field of Classification Search ................ 514/2, 514/16; 350/300, 329; 435/69.1; 530/300, 530/350

See application file for complete search history.

(56) References Cited

U.S. PATENT DOCUMENTS 6,248,319 B1 * 6/2001 Zsebo et al. ............... 424/85.1

FOREIGN PATENT DOCUMENTS

WO    WO 200188092    * 11/2001

OTHER PUBLICATIONS

Brannan et al., "Developmental Abnormalities in Steel$^{17H}$ Mice Result from a Splicing Defect in the Steel Factor Cytoplasmic Tail," *Genes & Development* 6:1832–1842 (1992).
Flanagan et al., "Transmembrane Form of the *kit* Ligand Growth Factor is Determined by Alternative Splicing and Is Missing in the $Sl^d$ Mutant," *Cell* 64:1025–1035 (1991).
Hellker et al., "Recognition of Sorting Signals by Clathrin Adaptors," *BioEssays* 21:558–567 (1999).
Huang et al., "Differential Expression and Processing of Two Cell Associated Forms of the Kit–Ligand: KL–1 and KL–2," *Molecular Biology of the Cell* 3:349–362 (1992).

Kapur et al., "The Presence of Novel Amino Acids in the Cytoplasmic Domain of Stem Cell Factor Results in Hematopoietic Defects in Steel$^{1TM}$ Mice," *Blood* 94:1915–1925 (1999).
Matter et al., "Structural Requirements and Sequence Motifs for polarized Sorting and Endocytosis of LDL and Fc Receptors in MDCK Cells," *The Journal of Cell Biology* 126:991–1004 (1994).
Motro et al., "Steel Mutant Mice are Deficient in Hippocampal Learning but not Long–Term Potentiation," *Proc. Natl. Acad. Sci. USA* 93:1808–1813 (1996).
Reich et al., "The Basolateral Sorting Signal of the Polymeric Immunoglobulin Receptor Contains Two Functional Domains," *Journal of Cell Science* 109:2133–2139 (1996).
Simmen et al., "The Tyrosinase Tail Mediates Sorting to the Lysosomal Compartment in MDCK Cells Via a Di–Leucine and a Tyrosine–Based Signal," *Journal of Cell Science* 112:45–53 (1999).
Simmen et al., "Basolateral Sorting of Furin in MDCK Cells Requires a Phenylalanine–Isoleucine Motif Together with an Acidic Amino Acid Cluster," *Molecular and Cellular Biology* 19:3136–3144 (1999).
Simonsen et al., "The Leucine–Based Motif DDQxxLI is Recognized Both for Internalization and Basolateral Sorting of Invariant Chain in MDCK Cells," *European Journal of Cell Biology* 76:25–32 (1998).
Tajima et al. "Role of Dimerization of the Membrane–Associated Growth Factor Kit Ligand in Juxtacrine Signaling: The $Sl^{17H}$ Mutation Affects Dimerization and Stability–Phenotypes in Hematopoiesis," *J. Exp. Med.* 187:1451–1461 (1998).
Wan et al., "PACS–1 Defines a Novel Gene Family of Cytosolic Sorting Proteins Required for Trans–Golgi Network Localization," *Cell* 94:205–216 (1998).
Wehrle–Haller et al., "Altered Cell–Surface Targeting of Stem Cell Factor Causes Loss of Melanocyte Precursors in Steel 17H Mutant Mice," *Developmental Biology* 210:71–86 (1999).

* cited by examiner

*Primary Examiner*—Jon Weber
*Assistant Examiner*—Sheridan K Snedden
(74) *Attorney, Agent, or Firm*—Clark & Elbing LLP

(57) ABSTRACT

Mono-leucine dependent basolateral sorting signal consisting of the amino acid sequence $X_1h_2X_3h_4Lp_5p_6$, wherein: $X_1$ represents a polar amino acid residue or alanine, $h_2$ represents any hydrophobic amino acid residue, $X_3$ represents any amino a residue, $h_4$ represents any hydrophobic amino acid residue, except leucine and isoleucine L represents a leucine residue, $p_5$ represents any polar amino acid residue, and $p_6$ represents any polar amino acid.

11 Claims, 13 Drawing Sheets

Figure 1:
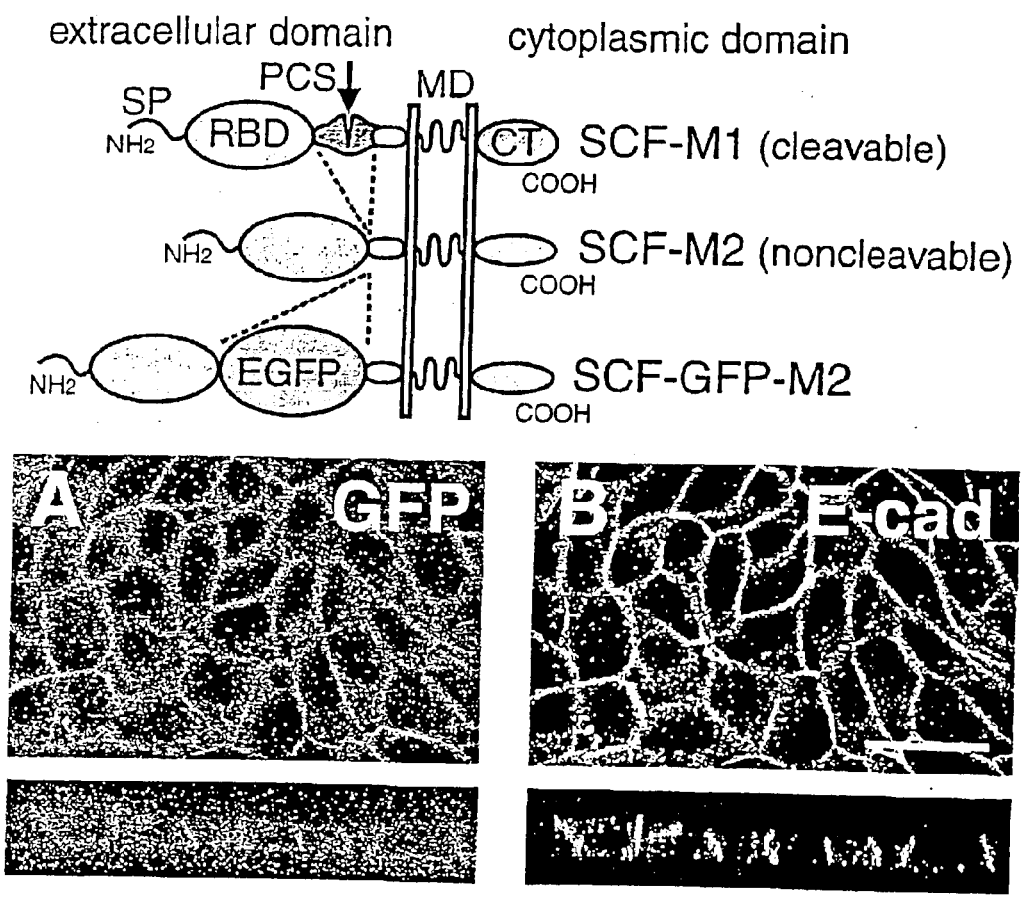

| Sequence (1-36) | Construct | Polarity | Distribution | Endocytosis |
|---|---|---|---|---|
| KKKQSSLTRAVENIQINEEDNEISMLQQKEREFQEV | wt | BL | S | – |
| KKKQSSLTRAVENIQINEEDNEISMLQQKEREFQE. | d36 | BL | S/I(ER) | – |
| KKKQSSLTRAVENIQINEEDNEISMLQQ...... | d29 | BL | S/I(ER) | + |
| KKKQSSLTRAVENIQINEEDN.......... | d22 | AP | S/I(ER) | – |
| KKKQSSLTRAV................... | d12 | AP | S/I(ER) | nd |
| KKKQSSLTRAV.........KEREFQEV | d21-28 | AP | S | nd |
| KKKQ................KEREFQEV | d12-28 | AP | S | nd |
| KKKQ..........NEISMLQQKEREFQEV | d5-20 | AP | S | nd |
| KKKQSSLTRAV...NEISMLQQKEREFQEV | d12-20 | BL/AP | S | nd |
| KKKQSSLTRAVENIQINEEDNEIAMLQQKEREFQEV | S24A | BL | S | nd |
| KKKQSSLTRAVENIQINEEDNEIDMLQQKEREFQEV | S24D | BL | S | nd |
| KKKQSSLTRAVENIQINEEDNEISMAQQKEREFQEV | L26A | AP | S | nd |
| KKKQSSLTRAVENIQINEEDNEISAAQQKEREFQEV | M25A/L26A | AP | S | nd |
| KKKQSSLTRAVENIQINEEDNEISALQQKEREFQEV | M25A | BL | S | nd |
| KKKQSSLTRAVENIQINEKDNEISMLQQKEREFQEV | E19K | BL | S | nd |
| KKKQSSLTRAVENIQINAAANEISMLQQKEREFQEV | E22A | BL | S | nd |
| KKKQSSLTRAVENIQINEEDNEIAMSQQKEREFQEV | E-D18A-A | BL/AP | S | nd |
| KKKQSSLTRAVENIQINEEDNEISLLQQKEREFQEV | S24A/L26S | AP | S | nd |
| KKKQSSLTRAVENIQINEEDNEISMLQQKEREFQEV | M25L | AP | S | nd |
| KKKQSSLTRAVENIQINEEDNEISMLQQKEREFQEQ | V36Q | BL | S/I(ER) | – |
| KKKQSSLTRAVENIQINEEDNEISMLQQKEREFQEVQ | add37Q | BL | S/I(ER) | – |
| KKKQSSLTRAVENIQINEEDNEISMAQQKEREFQE. | L26A/d36 | AP | S/I(ER) | – |
| KYAATERERISRGVIVDVSTLLPSHSGW | SCF-17H | nd | I(vesic) | ++ |
| KYAATERERISRGVIVDVSTAAPSHSGW | SCF-17H(L20A/L21A) | AP | S | – |
| QRRQRKSRRTIQASS | IL-2 receptor alpha chain (wt) | AP | S | nd |
| RLCLQKKKKKQPQERRQPLLMDKDDYHSLLYQSHL | tyrosinase | nd | I(vesic) | +++ |
| KWKWRSRDPQTLDSSVGRPEDSSLTQDEDRQVELPV | CSF-1 wt | BL/AP | S | nd |
| KWKWRSRDPQTLDSSVGRPEDSSATQDEDRQVELPV | CSF-1L24A | AP | S | nd |

FIGURE 2A

Transmembrane and Cytoplasmic Tail Sequences of Stem Cell factor

```
Human:      MALPALFSLIIGFAFGALYWKKKRQPSLTRAV.ENIQIN..EEDNEISMLQEKEREFQEV
Mouse:      MALPALISLVIGFAFGALYWKKKQSSLTRAV.ENIQIN..EEDNEISMLQQKEREFQEV
Dog:        MALPAFFSLVIGFAFGALYWKKKQPNLTRTV.ENIQIN..EEDNEISMLQEKEREFQEV
Horse:      MALPAFFSLVIGFAFGALYWKKKQPNLTRAV.ENIQIN..EEDNEISMLQEKEREFQEV
Cow:        VALPAFFSLVIGFAFGAFYWKKKQPNLTRTV.ENIQIN..EEDNEISMLQEK.......
Sheep:      VALPAFFSLVIGFAFGALYWKKKQPNLTRTV.ENRQIN..EEDNEISMLQEK.......
Cat:        MALPACFSLVIGFAFGALYWKKKQPNLTRTV.ENIQIN..EEDNEISMLQEKEREFQEV
Swine:      VALPAFFSLVIGFAFGALYWKKKQPNLTRTV.ENIQIN..EEDNEISMLQEKEREFQEV
Chicken:    IALTSLLSLLIGFILGAIYWKKTHPKSRPESNETIQCHGCQEENEISMLQQKEKEHLQV
Quail:      IALTSLLSLLIGFILGVIYWKKTHPKSRPESNETTQCHGCQEENEISMLQQKEKEHLQV
Salamander: VALISLSSLVLGFIIGVVCWKMKHRESGSGCEPTAPCPVRKEAEAEQASMLNQTGKAVHLV
Consensus:  -AL-----SL-IGF--G--YWKK---------E--Q-----E-NEISMLQ-KE-E---V
                 \ transmembrane \  cytoplasmic
```

FIGURE 2B

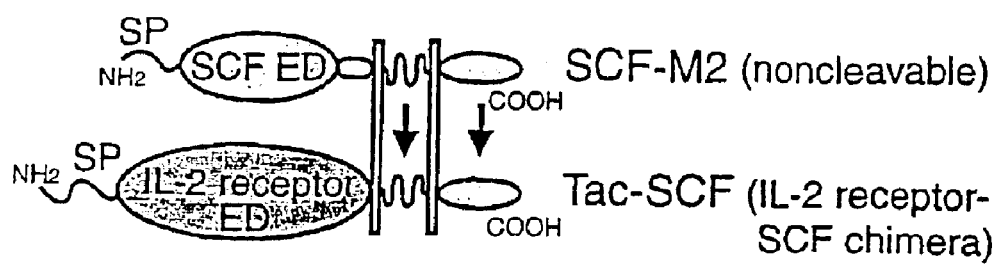
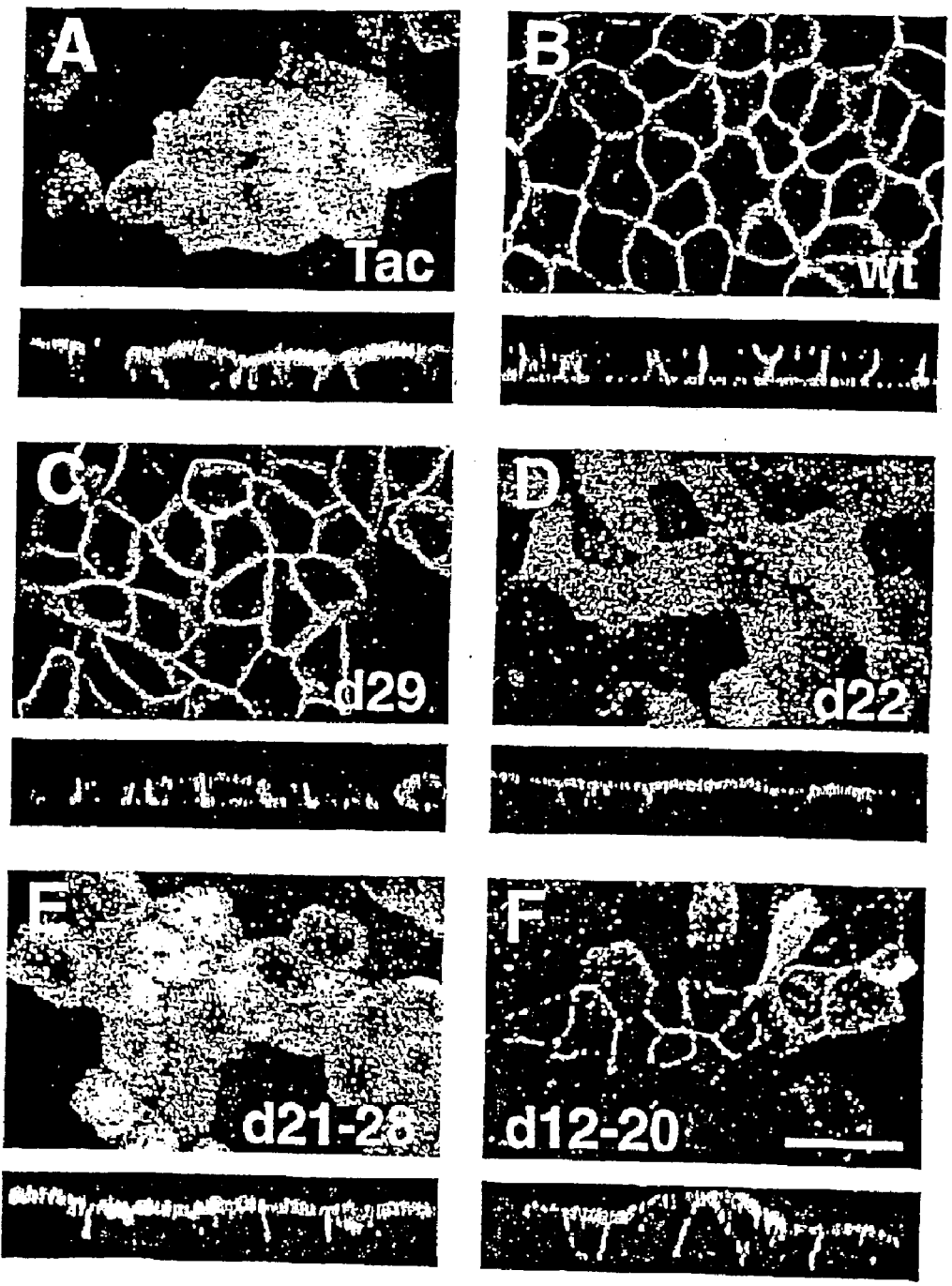
FIGURE 4

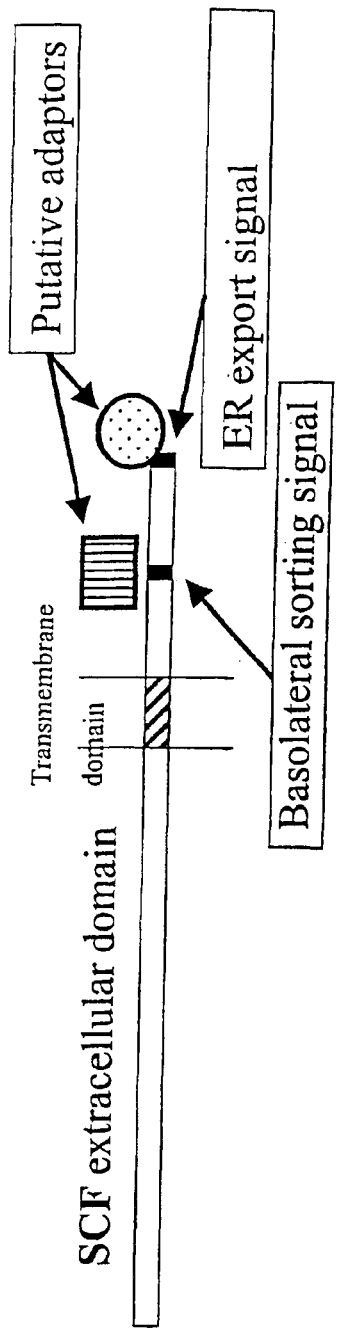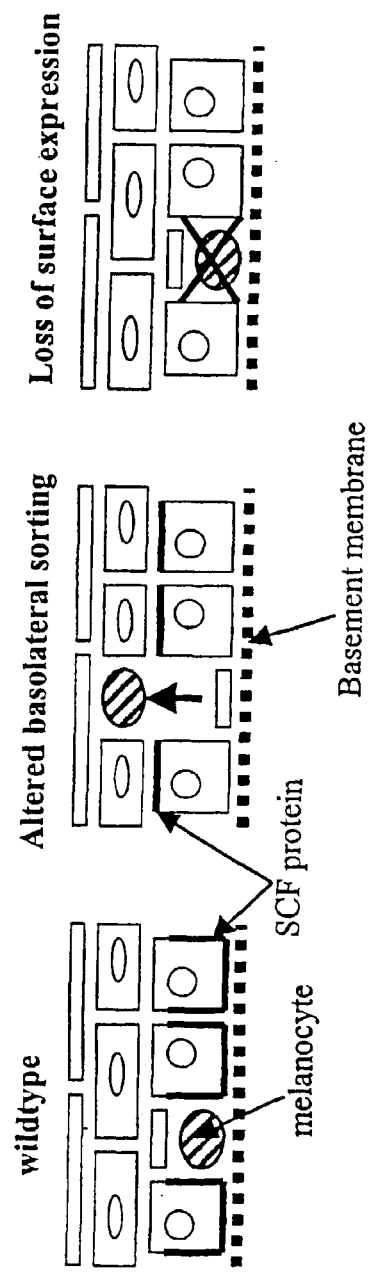
Figure 10

FIGURE 11

BASOLATERAL SORTING SIGNAL AND INHIBITORS THEREOF

CROSS REFERENCE TO RELATED APPLICATIONS

This application is a continuation of, and claims priority from, international application number PCT/EP00/13141, filed Dec. 22, 2000, which, in turn, claims priority from international application number PCT/CH99/00624, filed Dec. 23, 1999.

The present invention relates to the identification of a new determinant responsible for basolateral targeting and prolonged exposure of cell-surface-anchored growth factors at cell surfaces. The invention also relates to molecules which modulate cell-surface expression by inhibition of basolateral targeting. The invention further concerns methods for modulating cell-surface expression in therapeutic, cosmetic and diagnostic settings.

More particularly, the invention further relates to efficient control of Stem Cell Factor (SCF) presentation in tissue, in order to exploit the correlation between the dose and localization of SCF and the amount of c-kit expressing cells in the tissue.

Stem Cell factor (also known as mast cell growth factor MGF, kit-ligand KL and Steel factor Sl) belongs to the family of cell surface anchored growth factors, including CSF-1, TGFα and TNFα. SCF is the ligand for the receptor tyrosine kinase encoded by the c-kit proto-oncogene, forming a monospecific receptor ligand pair. It has been identified and cloned by several laboratories in 1990.

SCF is expressed as two alternatively-spliced membrane bound forms (M1 and M2) with a type I transmembrane topology, distinguished by an exon containing a proteolytic cleavage site in the M1 form. This site is used to generate soluble growth factor from the M1 membrane bound precursor. After synthesis in the endoplasmic reticulum, SCF associates to form non-covalently bound dimer and is expressed on the cell surface. Both membrane-bound versions M1 and M2 can mediate direct cell-cell contact with c-kit expressing cells, e.g. bone marrow-derived mast cells, melanocytes and primordial germ cells. Proteolytic processing of both membrane-bound versions releases biologically active soluble SCF proteins. Like several cytokines and/or growth factors, such as colony-stimulating facor-1 (CSF-1), these ligands are active as membrane bound as well as proteolytically shed products.

SCF is delivered directly to the basolateral cell surf ace in epithelial cells and does not accumulate in an intracellular compartment (8). Consequently, SCF remains at the cell surface until the extracellular domain is proteolytically shed within 0.5 (M1) to 5 (M2) hours depending on the respective splice form (20).

The primary sequence of SCF consists of a signal peptide followed by a globular c-kit binding domain of about 150 amino acids. Between this globular domain and the transmembrane segment, there is a linker region of variable length due to alternative splicing. The proteolytically cleaved extracellular domain consists of 164 amino acids.

SCF can promote several distinct biological functions. SCF can induce proliferation, survival, adhesion/migration and differentiation in c-kit expressing cells of hematopoietic and non-hematopoietic lineages.

This protein has already been identified in several different organisms, particularly in human, mouse, chicken, cat, dog, horse, cow, sheep, swine, quail, rat and salamander. The sequences are well conserved between species, especially the cytoplasmic domain which is highly conserved. But homologies are also be found with other transmembrane growth factors such as colony-stimulating facor-1 (CSF-1).

SCF is expressed in numerous different type of cells and its roles are also numerous. The influence of SCF on the pigmentation is the best known and the first to have been studied as being responsible for the white spotting phenotype. The role of SCF in keratinocytes has been extensively studied by the applicant.

SCF is brought to the basolateral surface of keratinocytes, from which a soluble ligand is produced by proteolysis. On the surface of melanocytes, SCF binds to a receptor tyrosine kinase (c-kit) which induces melanocyte proliferation, survival and migration in vivo and in vitro. Furthermore, transcription factors critical for the expression of melanin producing enzymes are activated by SCF/c-kit signaling.

An important role for SCF in maintaining melanocytes in the epidermis has recently been corroborated by studies in mice. SCF is normally downregulated in the interfollicular epidermis of mouse skin, which is reflected by the absence of epidermal melanocytes. Transgene expression of SCF in the basal layer of the epidermis rescues the loss of melanocytes from this region of the epidermis. Although the skin of adult mice can not be compared with the human skin, many important SCF activities on melanocytes can be inferred from analysis of mouse embryos mutant for different alleles of the SCF gene. Based on these studies, the applicant concluded that melanocyte migration follows the localization and presentation of SCF, while melanocyte proliferation is proportional to the amount of SCF expressed in the epidermis. A similar correlation has been established for mastocytes in the dermal mesenchyme.

Molecular characterization of various Mgf alleles has provided important insight into the role of the soluble and membrane-anchored forms of SCF. These mutants profoundly affect the development of three seemingly unrelated stem cell populations, neural crest-derived melanocytes, germ cells and hematopoietic precursor cells.

Molecular analysis of the Steel-Dickie mutation ($Sl^d$ or $Mgf^{Sld}$) showed an intragenic deletion including the transmembrane domain and COOH terminus, generating a secreted SCF protein product with normal biological activity. Homozygotes for the $Mgf^{Sld}$ mutation are viable but severely affected. The membrane anchor of SCF is required for its biological activity in vivo, since the expression of only the extracellular receptor binding domain leads to the loss of SCF dependent cells affecting skin pigmentation, sterility, hematopoiesis and learning (3-4).

The $Sl^{17H}$ allele or $Mgf^{Sl17H}$, contains a point mutation, which results in the skipping of the exon coding for the cytoplasmic tail of mouse SCF. The cell populations affected by altered $Sl^{17H}$ consists of peripheral mast cells, primordial germ cells, spermatogonia in the testis and oogonia in the ovaries, neural crest derived melanocytes in the skin and inner ear, hematopoietic stem cells in the bone marrow, T-cell precursors from the bone marrow and the pacemaker system along the gut. This mutation thus leads to an altered cytoplasmic sequence which abrogates coat pigmentation, male fertility and reduces hematopoiesis (5-7). In this mouse mutant, cell surface expression of SCF is reduced and basolateral sorting in epithelial tissues is lost (8).

Whilst these results provide preliminary indications that the cytoplasmic tail of SCF may harbor information required for efficient cell surface presentation and basolateral targeting, the precise sequences and mechanisms responsible for this essential property remain unknown.

In this respect, it is noteworthy that a number of different sorting determinants have already been identified in some classes of protein, including signals involved in the transport of newly synthesized membrane proteins from the trans-Golgi network to the basolateral surface (refs 11, 16, 17). However, these basolateral targeting signals generally contain a critical tyrosine, di-leucine or di-hydrophobic motif. SCF does not contain a functional equivalent of these typical sorting sequences in its cytoplasmic tail, suggesting that it represents a new class of basolaterally targeted molecule.

To date, the precise role played by the cytoplasmic tail in cell surface presentation of SCF, and the extent of involvement of other molecules, or other intermolecular interactions, remains to be elucidated. Since basolateral expression and retention of SCF are functions which are absolutely required to fulfill its function in vivo, the lack of knowledge regarding the responsible mechanisms and signals has prevented progress in the development of therapeutic, diagnostic and cosmetic agents modulating cell-surface expression.

The present inventors have analysed the cytoplasmic domain of SCF for the presence of intracellular targeting determinants required for basolateral and cell surface expression of the transmembrane SCF precursor and for cell surface retention. In this context, a targeting signal which exhibits some similarities to a di-leucine based signal otherwise responsible for basolateral targeting as well as endocytosis, has been identified. A point mutation in this sequence is sufficient to redirect mutant SCF precursor molecules to the apical surface of epithelial cells.

To study the targeting of SCF, reporter constructs were used consisting of extracellular green fluorescent protein (GFP) tagged SCF or chimeras of the extracellular domain of the interleukin-2 receptor α-chain (Tac) fused to the transmembrane and cytoplasmic sequences of SCF. In these chimeras the normal intracellular domain of SCF is left intact, allowing optimal interaction of the latter with the sorting machinery of polarized cells and the identification of critical targeting domains by mutagenesis.

The inventors have also identified critical residues required for the prevention of internalisation of SCF. When the cytoplasmic tail is mutated, as in $Mgf^{S17H}$ mutation, SCF is efficiently removed from the cell surface by endocytosis. Accordingly, constant endocytosis reduces the steady state level of surface expressed SCF to an extent detectable by a change in melanocyte number.

In conclusion, by analysing wildtype and cytoplasmic mutant chimeras in epithelial and fibroblastic cells, a novel motif has been identified in a transmembrane growth factor that is used for basolateral targeting and which maintains membrane expression by preventing endocytosis, not allowing or not inducing endocytosis. A critical leucine residue is required for basolateral targeting of SCF. The efficiency of the targeting is enhanced by the presence of an acidic cluster Moreover, based on functional similarities and sequence comparison with other transmembrane growth factors like CSF-1, it is proposed that the basolateral determinant and associated functions are not unique to SCF, but are common to other cell-surface anchored growth factors having a similar single leucine in the cytoplasmic domain.

The identification of this novel motif provides a basis for a completely new approach to alter the behaviour of cells expressing these cell-surface growth-factors, for example melanocyte and mastocyte behavior in the epidermis and dermis respectively. By peptide analog interference of specific cytoplasmic targeting sequences in Stem Cell Factor expressed in basal keratinocytes and dermal fibroblasts, it is proposed to alter the behavior of melanocytes and mastocyte (number and localization) which express the receptor for this growth factor. These findings are relevant to pigmentation, fertility and hematopoietic defects.

A first aspect of the invention involves a novel basolateral sorting signal comprising as an essential part, a leucine residue.

Based on the study of SCF and the environment of the novel basolateral sorting signal in this protein, a second aspect of the invention involves proteins or peptides comprising this signal and the properties conferred by this signal.

A third aspect of the invention relates to inhibitors of the basolateral sorting and surface retention in a cell. Screening methods for identifying such inhibitors are also described.

A fourth aspect of the present invention relates to the use as medicament of the peptides according to the second aspect or of inhibitors according to the third aspect.

In the context of the present invention, the following terms are to be understood by the following definition:

A polarized cell is defined by the properties of its plasma membrane, such as epithelial cells, neurons. The plasma membrane of polarized cells is divided into apical and basolateral domains with distinct protein and lipid compositions. In polarized cells, e.g. in MDKC (Madin Darby Canine Kidney cells), basolateral sorting of transmembrane proteins takes place in the trans-golgi network (TGN) or endosomal compartments.

A basolateral sorting signal is a sequence of amino acids within a protein which is essential for the targeting of the protein to the basolateral membrane in a polarized cell. The signal may reside in a single amino acid motif, or may be composed of two or more distinct motifs within the protein. Preferably, the basolateral sorting signal is essential and sufficient for basolateral targeting of the protein, although the presence of other sequences, for example an acidic cluster, may enhance the efficiency of the sorting. The basolateral sorting signal may further have additional functions, such as the capacity to induce endocytosis of the protein (11). In accordance with the invention, these additional functions may include the capacity to prevent endocytosis of the protein.

By nucleic acid molecule, it is meant a sequence of nucleotides which can be deoxyribonucleotides, dideoxyribonucleotides or a mixture thereof. A nucleic acid molecule can thus be a DNA fragment, single or double-stranded, an RNA fragment, or a hybrid molecule. This hybrid molecule can be for example a single stranded DNA hybridized with an RNA molecule.

A first nucleic acid molecule is said to be complementary to a second nucleic acid molecule when the first molecule can form Watson-Crick base pairs with the second molecule along at least part of its length. Adenine pairs with Thymine or Uracil, and Guanine pairs with Cytosine. A single stranded DNA molecule can be complementary to an RNA molecule, provided the preceding correspondence is respected.

In accordance with the present invention, amino acids are classified according to their properties. By basic amino acid, is meant a lysine or an arginine. These amino acids are also classified as positively charged amino acids. By acidic amino acid, is meant an aspartic acid or a glutamic acid. These amino acids are also classified as negatively charged amino acids. The preceding four amino acids are charged amino acids.

By a small apolar amino acid, is meant a glycine, an alanine, a proline, a cystein or a valine. By large apolar amino acid, is meant a leucine, an isoleucine, a phenylalanine, a methionine or a tryptophane. The term apolar amino acid has the same meaning as hydrophobic amino acid. By very hydrophobic amino acid, is meant a phenylalanine, a leucine or an isoleucine. The very hydrophobic amino acids are the large apolar ones.

By a small polar amino acid, it is meant a serine or a threonine. By large polar amino acid, is meant an asparagine or a glutamine. Tyrosine can also be classified as polar.

By aromatic amino acids, is meant a tyrosine, a phenylalanine or a tryptophane.

The above described properties of amino acids are conserved when they are inserted into a peptide.

An acidic cluster according to the invention is a sequence of consecutive amino acids in which half or more of the residues have acidic properties. According to this definition, all the amino acids present in an acidic cluster according to the invention are not necessarily acidic. Acidic amino acid are glutamic acid and aspartic acid. An acidic cluster can be constituted by at least two amino acids, for example two to eight or ten amino acids.

A cytoplasmic protein is a protein which is in the cytoplasm of the cell in which it is expressed. Generally speaking, all proteins can be considered as cytoplasmic immediately after synthesis and before insertion into the membrane, secretion, proteolysis etc. . . . By cytoplasmic protein it is thus preferably meant a protein which stays in the cytoplasm of the cell in which it is expressed. According to the invention, cytoplasmic proteins are thus intracellular proteins. Preferably, a cytoplasmic protein remains soluble and does not form inclusion bodies.

A soluble protein is not bound in the membrane of the cell in which it is expressed. A soluble protein is either secreted into the extracellular medium or stays in the cytoplasm of the cell.

Membrane-, transmembrane-, membrane anchored- and membrane bound-proteins are proteins having at least one domain with an affinity for the membrane of the cell in which it is expressed. More particularly, a transmembrane protein has at least one domain which is specifically inserted into the membrane. This transmembrane domain (TMD) has a very specific amino acid composition and structure allowing it to span the very hydrophobic environment constituted by the lipids of the membrane. A membrane protein may span the membrane several times.

In the context of the present invention, by transmembrane protein is meant a membrane protein having a single TMD. As a result, this type of protein has a terminus in the intracellular compartment and the other one in the extracellular compartment. The domain of the protein staying in the cytoplasm of the cell is referred to as the cytoplasmic domain or cytoplasmic tail, the domain on the other side of the membrane is referred as the extracellular domain or extracellular tail. This protein is either of type I topology if its C-terminus is intracellular or of type II topology if its N-terminus is intracellular.

A protein can be considered as having a cytoplasmic domain if at least one domain of its structure remains in the cytoplasm of the cell in which it is expressed. Preferably, this expression is used for defining the domain of a transmembrane protein which remains in the intracellular compartment.

The different aspects of the invention will be described in detail below.

According to a first aspect, the present invention describes a novel basolateral sorting signal consisting of seven consecutive amino acids. This signal is dependent on a single hydrophobic leucine, unlike known di-leucine or leucine-isoleucine motifs which require two consecutive very hydrophobic amino acids. The basolateral sorting signal according to the invention is thus designated as "mono-leucine dependent".

More specifically, the mono-leucine basolateral sorting signal of the invention can be represented by the general formula (I):

$$X_1 h_2 X_3 h_4 L{+}ee\ p_5 p_6 (\text{SEQ ID NO: 1}), \qquad (I)$$

wherein:
  $X_1$ represents a polar amino acid residue or alanine,
  $h_2$ represents any hydrophobic amino acid residue,
  $X_3$ represents any amino acid residue,
  $h_4$ represents any hydrophobic amino acid residue, except leucine and isoleucine
  L represents a leucine residue,
  $p_5$ represents any polar amino acid residue, and
  $p_6$ represents any polar amino acid.

The folding of this signal probably results in the leucine being exposed at the surface of the tri-dimensional structure. The heptapeptide signal is preferably devoid of proline, which is known to form a kink in the structure because of its cyclic side chain, and is thus likely to destroy the structure of the signal.

The signal of the invention may have a linear or a cyclic structure.

In another preferred embodiment of this formula, $X_1$ represents a glutamic acid, a glutamine or an alanine residue, $h_2$ represents an isoleucine or an alanine residue, $X_3$ represents a serine, an alanine or an aspartic acid residue, $h_4$ represents a methionine or an alanine residue, $p_5$ represents a glutamine or an asparagine residue, and $p_6$ represents a glutamine or a glutamic acid residue.

In a most preferred embodiment of this first aspect of the invention, the formula is centered on the basolateral sorting signal identified by the inventors in SCF. This signal identified in mouse SCF has the particular sequence EISMLQ.

In the general formula I above, the elements ($X_1$; $h_2$; $X_3$; $h_4$; $p_5$; $p_6$) are variable, the others being constant. According to a preferred embodiment, the class of molecules represented by the general formula I thus comprises the following sub-classes, wherein ($X_1$; $h_2$; $X_3$; $h_4$; $p_5$; $p_6$) have the following signification:

(any amino acid; I; S; M; Q; Q or E) or
  (E; any hydrophobic amino acid; S; M; Q; Q or E) or
  (E; I; any amino acid; M; Q; Q or E) or
  (E; I; S; any hydrophobic amino acid except L and I; Q; Q or E) or
  (E; I; S; M; any polar amino acid; Q or E) or
  (E; I; S; M; Q; any polar amino acid).

In this respect, in accordance with the invention, amino acids are represented using the single-letter amino acid code.

According to a particularly preferred embodiment, in the general formula (I) ($X_1$; $h_2$; $X_3$; $h_4$; $p_5$; $p_6$) represents (E or Q; I or A; S; M; Q or N; E or Q).

For example, according to this embodiment, the basolateral sorting signal is selected from the following heptapeptides (SEQ ID NOS: 2–18): EISMLQQ, EISMLQE, AISMLQQ, AISMLQE, QISMLQQ, QISMLQE, EASMLQQ, EASMLQE, EIDMLQQ, EIDMLQE, EIAMLQQ, EIAMLQE, EISALQQ, EISALQE, EISMLNQ, EISMLNE, and QASMLNQ.

According to a second aspect, the invention relates to peptides or proteins which comprise the mono-leucine basolateral sorting signal as described above.

An example of a peptide according to this variant of the invention, is an octapeptide composed of an asparagine amino acid residue followed by the heptapeptide signal of the invention, and peptides and proteins comprising this octapeptide, particularly those having a length of at least 10 amino acids, for example at least 11 or at least 12. They may have upto about 500, for example 100–300 amino acids.

This aspect of the invention also concerns peptides which are composed of the seven amino acids forming the signal according to the first aspect of the invention, followed by 1, 2 or 3 polar amino acids. These residues can be for example glutamine residues.

The proteins or peptides according to this aspect of the invention can be naturally occurring, chimeric peptides or synthetic compounds. When the invention concerns naturally occurring proteins said proteins do not comprise full-length human, mouse, chicken, cat, dog, horse, cow, sheep, swine, quail, rat or salamander SCF, present in the database Genbank under accession numbers M59964 for human, M57647 and U44725 for mouse, D13516 for chicken, D50833 for cat, S53329 for dog, AF053498 for horse, D28934 and AB033716 for cow, U89874 for sheep, L07786 for swine, U43078 for quail, AF071204 for rat and AF119044 for salamander.

Analysis of the SCF cytoplasmic domain has revealed an acidic cluster comprising the sequence "EED" 8 residues upstream of the leucine of the basolateral sorting signal of the invention. Indeed, many di-leucine sorting motifs have been described which require critical N- or C-terminally located acidic residues as described for the furin protease (25), the LDL receptor (16) and the Invariant chain of MHC II (17). Members of the recently identified phosphofurin acidic cluster-sorting (PACS) family of adaptor proteins which bind to clusters of acidic amino acids are involved in directing TGN localization and plasma membrane sorting (19). Interestingly, intracellular sorting of the furin protease by PACS is regulated by the phosphorylation of critical serine residues adjacent to a cluster of acidic amino acids. The same PACS binding, acidic cluster which directs TGN localization, is also required for basolateral sorting of furin (25).

Although PACS may bind to the acidic amino acid cluster in SCF and thereby increase the fidelity of the basolateral sorting process in the TGN, there is no indication that this is a phosphorylation dependent interaction involving the conserved serine residue at position −2 with respect to the leucine.

Consequently, according to a first variant of this second aspect of the invention; the mono-leucine dependent basolateral sorting signal is accompanied by an acidic cluster.

This acidic cluster is required for efficient basolateral sorting. While the leucine is indispensable for basolateral transport, the presence of the acidic cluster enhances the efficiency of basolateral sorting. In contrast to other known basolateral determinants, in which the acidic amino acids are essential for basolateral targeting, the acidic cluster in the basolateral sorting signal of the invention is partially dispensable, but serves however to increase the fidelity of the basolateral sorting process.

In the absence of such N-terminal located acidic clusters (as in the cytoplasmic tail of CSF-1), reduced protein recognition at the level of the TGN could thus give rise to less efficient basolateral targeting compared to cytoplasmic tails comprising such acidic clusters, like SCF. This inefficiency of basolateral sorting may lead to the apical accumulation of CSF-1 by an N-glycan dependent apical targeting pathway.

Since the acidic cluster is not absolutely required for basolateral targeting, the two motifs do not form a single sorting determinant. Preferably, if the two motifs are naturally occurring in a peptide or a protein, they are encoded on two different exons. They can also be encoded by the same exon.

Preferably, the acidic cluster comprises at least two acidic amino acids, selected from glutamic acid and aspartic acid.

In a preferred embodiment, the acidic cluster comprises the sequence ExE, ExD, DxE or DxD, wherein x is any amino acid. Preferably, the amino acid sequence is EED, or QEE, or EAE, or EKD, where E represents a glutamic acid residue, Q a glutamine residue, D an aspartic acid residue and A an alanine residue.

In a peptide or protein comprising the basolateral sorting signal and an acidic cluster according to the present invention protein, said acidic cluster is preferably N-terminal to the basolateral sorting signal. Particularly preferred peptides or proteins comprise the acidic clusters EED, or QEE, or EAE, positioned N-terminal to any one of the basolateral sorting motifs EISMLQQ, EISMLQE, AISMLQQ, AISMLQE, QISMLQQ, QISMLQE, EASMLQQ, EASMLQE, EIDMLQQ, EIDMLQE, EIAMLQQ, EIAMLQE, EISALQQ, EISALQE, EISMLNQ, EISMLNE, and QASMLNQ (SEQ ID NOS: 2–18). Most preferably, these proteins or peptides further comprise an asparagine (N) or a glutamic acid residue positioned immediately between the acidic cluster and the sorting signal.

In another embodiment, peptides or proteins according to the present invention may further comprise a cluster of at least four consecutive charged amino acids. These charged amino acids are chosen among aspartic acid, glutamic acid, lysine, arginine and histidine. Because histidine can be charged or neutral at physiological pH, this amino acid is preferably excluded from the selection of charged amino acids. Since the positively charged amino acids have also basic properties and the negatively ones have acidic properties, this cluster of charged amino acids can also be considered as a cluster displaying acido-basic properties.

In a preferred version of this charged cluster, the four consecutive amino acids are alternatively positively and negatively charged or alternatively acidic and basic. Some preferred examples of such a cluster include the amino acid sequences KERE, KEKE, DEDR or EEDR (SEQ ID NOS:19, 20, 75, 21) where K represents a lysine residue, E a glutamic acid residue, R an arginine residue and D an aspartic acid residue.

Other clusters are possible, especially clusters in which the second or third amino acid of the four is neutral, provided only one of four has no charge. This cluster can effectively be considered as charged according to the present invention because the number of charges per residue in the cluster is superior to the mean number of charge per residue in a random polypeptide.

In a preferred embodiment of the invention, this additional charged cluster is C-terminal to the basolateral sorting signal of the invention.

It is worth noting that this second cluster can be also an acidic cluster according to the definition given above. In this respect, the basolateral sorting signal can be positioned between two different acidic clusters.

In another embodiment, a peptide or protein according to the present invention further comprises a valine at its C-terminus. The applicant has compared the cytoplasmic tail of CSF-1 and SCF and has identified a conserved C-terminal valine residue. Based on sequence comparison with SCF and the data presented below in the experimental section, it appears that this C-terminal valine is important for the efficient export of CSF-1 and SCF from the endoplasmic reticulum (ER) to the Golgi and cell surface. All mutant constructs lacking the C-terminal valine are retained in the ER and cell surface transport is delayed and occurs through the bulk protein flow from the ER to the cell surface. Therefore, absence of this valine determinant results in a reduced expression of the protein or peptide of the invention at the cell surface.

The role of this valine residue can be generalized to the mono-leucine basolateral sorting signal of the invention of which SCF and CSF-1 are preferred embodiments.

Interestingly, a basolateral targeting motif has been described for the polymeric Ig receptor which does not belong to the family of tyrosine or di-leucine determinants and which does not mediate endocytosis. This critical targeting domain consists of a single valine located in a β-turn and two critical residues 3 and 4 amino acids N-terminal to it. Mutation of valine to alanine reduces basolateral targeting and destabilizes the β-turn (35). In addition, the amino acids N-terminal to the valine which do not participate in the β-turn are also required for efficient basolateral sorting and form a second, valine independent, functional targeting domain (35). Based on these similarities, it is possible that leucine 26 of SCF is part of a β-turn, loop or an alpha-helix, exposing its hydrophobic side chain in such a way that it could bind to the adaptor complex of clathrin coated vesicles.

Based on these data, a peptide or protein comprising the signal peptide of the invention adopts preferably a structure exposing the hydrophobic side chain of the leucine in such a way that it could bind to the adaptor complex of clathrin coated vesicles.

In a preferred embodiment, a peptide or protein according to the present invention comprises all the necessary information to be expressed in a cell. If the peptide is encoded by a nucleotide sequence which is heterologous to the cell, this sequence is introduced into a cell being capable of translating the information encoded by the nucleotide sequence and capable of synthesizing the corresponding peptide. Preferably, this peptide possesses at least one cytoplasmic domain.

A particularly advantageous embodiment of the invention is a protein or peptide comprising the basolateral sorting signal in its cytoplasmic domain, and further comprising at least one transmembrane domain or membrane anchor.

Preferably, this protein or peptide comprises a single transmembrane domain and the sorting signal is present within the cytoplasmic tail of the protein. The position of the basolateral sorting signal within the cytoplasmic tail is of importance. Indeed, as discussed above, the structure of the basolateral sorting signal appears to play a role in the targeting. The crucial leucine is very probably exposed at the surface of this structure. As the leucine is a hydrophobic residue, exposure of this amino acid at the surface is energetically unfavorable for the protein. The local structure of the signal provides the energy required by the exposure. It is thus important to preserve a position of the signal permitting this particular structure.

In this respect, the basolateral signal is preferably not positioned directly after the transmembrane domain. Effectively, such a position would mean a reduced number of possibilities for the conformation of the signal due to mechanical and energetic constraints imposed by the proximity of the membrane and the polar heads of the lipids. Presence of a flexible spacer between the transmembrane domain and the basolateral sorting signal of the invention, although not strictly required, can be very advantageous. Preferably, this spacer has no particular structure. In a particularly preferred variant, the leucine in the basolateral sorting signal is positioned between 15 and 35 amino acids from the transmembrane domain. The end of the transmembrane domain can be established without difficulty by programs of amino acid sequence analyzers.

In a preferred embodiment of the invention, peptides or proteins comprising the basolateral sorting signal of the invention, when they are expressed in a polarized cell, are targeted to the basolateral membrane of the cell. Polarized cells include Sertoli cells, keratinocytes, lung epithelial cells, kidney epithelial cells, endothelial cells from skin, from respiratory and alimentary tract, from aorta, from bone marrow, osteoblasts, thymic epithelial cells, ovaries cells, and neurons expressing SCF. Typical examples of polarized cells used in accordance with the invention are epithelial cells such as MDCK cells.

According to the present invention, the basolateral signal functions as an addressing signal to the basolateral membrane of polarized cells, when it is present in the cytoplasmic domain of a membrane protein. As discussed above; this signal must be in a position allowing it to fulfill its sorting function. According to the invention, this sorting is accomplished irrespective of the nature of the extracellular domain of the protein or peptide in the cytoplasmic tail of which the signal is present. Moreover, it is independent of the transmembrane domain of the peptide or protein. In a preferred embodiment already mentioned, it is also independent of the other residues of the cytoplasmic tail of said protein or peptide.

The basolateral signal of the invention as defined by General formula (I) and its preferred embodiments, can have two functions, i.e. targeting to the basolateral membrane, and/or limitation or prevention of endocytosis from the cell membrane. In the following, these functions will be designated "Function A" (addressing to the basolateral membrane), and "Function B" (limiting internalization by endocytosis from the cell membrane).

In order to display Function A, the basolateral sorting signal must be present within a membrane protein, in the particular molecular environment described above, and expression must be in a polarized cell. As discussed earlier in detail, the presence of other conditions may also be required to enhance the efficiency of sorting, for example the presence of an acidic cluster, and/or the presence of a further charged cluster, and the presence of a C-terminal valine.

The conditions required for the implementation of Function B are the same as for the Function A, except that expression is not necessarily in a polarized cell, and the presence of the C-terminal valine is more critical. The experimental section below provides examples of the consequences of Function B.

A peptide or protein comprising the basolateral signal of the invention has preferably a cytoplasmic domain according to the general formula:

$$z\text{-}(X)_p\text{-}Acc\text{-}(X)_q\text{-}(Ba)\text{-}(X)_r\text{-}(V)_f \qquad (II)$$

wherein:
each X independently represents an amino acid residue;
z represents a lysine (K) or an arginine residue (R);

p represents an integer from 12 to 22;

q represents 0 or an integer from 1 to 4;

r represents an integer from 2 to 12;

"Acc" represents an acidic cluster;

"Ba" represents the basolateral sorting signal according to any one of claims 1 to 5;

V represents a valine residue;

f represents 0 or 1, and wherein the multiple amino acid residues represented by (X) can be the same or different.

In a most preferred embodiment, a peptide or protein as described has a cytoplasmic domain sharing high identity with the amino acid sequence of the cytoplasmic tail of human, mouse, chicken, cat, dog, horse, cow, sheep, swine, quail, rat or salamander SCF, as illustrated in FIG. 2B. By high identity is meant a sequence exhibiting at least 80%, preferably at least 90% and most preferably at least 95% identity with the illustrated cytoplasmic domains.

The present invention also relates to nucleic acid molecules encoding a peptidic basolateral sorting signal as described by the general formula (I) as well as in the preferred embodiments of this formula. The invention also relates to nucleic acid molecules encoding a protein or peptide comprising the basolateral sorting signal of the invention.

The invention also relates to a nucleic acid molecule which is complementary to a nucleic acid molecule according to the preceding description.

The nucleic acids of the invention include vectors for expression in prokaryotic and eukaryotic cells, chimeric genes including regulatory signals appropriate for expression in desired cell types, antisense and ribozyme sequences.

The present invention also encompasses cells which express a peptide or protein comprising the basolateral sorting signal of the invention. This peptide or protein can be expressed from a DNA or an RNA molecules. Such molecules can be resident in the cell or can be introduced. The introduction can be made by any of the techniques conventional in the art, for example by electroporation, microinjection or by use of a recombinant virus etc. . . .

The invention also relates to a cell containing a nucleic acid encoding the signal peptide of the invention, or a peptide or a protein as they are described above. This nucleic acid can be endogenous to the cell, or heterologous to the cell. It can be introduced into the cell using the techniques mentioned above. The nucleic acid molecule can be naked or in a complex to improve efficiency of introduction and survival in the cell. This nucleic acid sequence can be part of a plasmid or of another vector. This vector preferably contains all the information necessary for the expression of the nucleic acid molecule.

The cells of the invention are preferably eukaryotic cells, particularly mammalian and most particularly human cells. Other examples of suitable mammalian cells are mouse, rat, monkey, hamster, dog, horse, cat etc. Plant cells are also encompassed by the invention, and prokaryotic cells such as bacterial are also contemplated.

In a preferred variant, the cells of the invention are polarized, as for example an MDCK cell or other epithelial cells, and Sertoli cells, keratinocytes, lung epithelial cells, kidney epithelial cells, endothelial cells from skin, from respiratory and alimentary tract, from aorta, from bone marrow, osteoblasts, thymic epithelial cells, ovaries cells, and neurons expressing SCF.

The properties of the cells expressing the peptides or proteins of the invention vary according to the precise nature of the protein or peptide expressed, and according to whether the cell is polarized, and whether it already expresses a basolaterally targeted protein. For example, a polarized cell expressing a transmembrane protein of the invention will be characterised by the surface expression of the protein specifically in the basolateral membrane. The same protein expressed in a non-polarized cell will be characterised by a non-specific surface expression of the protein. Polarized cells which already express an endogenous basolateral protein and which are transformed to express a heterologous protein of the invention will generally be characterised by a reduction in the basolateral expression of the endogenous protein, and possibly by the appearance of apical expression of the endogenous protein.

In a third aspect, the invention relates to inhibition of polarized as well as cell surface expression.

Based on the data of the experimental section as well as inferred from targeting data obtained in other experimental systems, the inventors postulate the presence of different adapter proteins which can specifically recognize targeting determinants present in the cytoplasmic tail of soluble or membrane proteins. It has been demonstrated in other systems, that such adapter proteins show a high degree of binding specificity towards one or the other of similar but not identical targeting sequences.

There are different classes of inhibitors according to the present invention.

Firstly, there are the competitive inhibitors. All peptide based or synthetic compounds that mimic the identified basolateral as well as C-terminal valine determinant, in an attempt to block the recognition of the latter by the cellular machinery. These inhibitors may be membrane permeable, cytoplasmic soluble, membrane anchored or a combination of the above.

Indeed, the results obtained in the present invention show that short peptide sequences having or comprising the general formula (I) could compete for binding of SCF to its specific adapter proteins, without blocking the entire intracellular protein transport of cells, for example in polarized cells like keratinocytes. Therefore, the introduction of such peptides into cells, for example into keratinocytes would modify the polarized surface expression of peptides or proteins comprising this basolateral signal determinant, for example modifying the polarized surface expression of SCF in keratinocytes and hence would alter melanocyte number and localization in the epidermis. Similarly, mastocytes localized in the dermis also depend on SCF presentation. A reduction of cell surface associated SCF induced by peptide analogs would also reduce the number of mastocytes in the skin.

According to a first embodiment, the inhibition of polarized as well as cell surface expression of SCF and SCF-like proteins is obtainable by the overexpression in a cell of a peptide analog. This overexpressed peptide analog saturates the pathways allowing basolateral sorting. The basolateral sorting is thus perturbed, leading to an apical expression for proteins which are normally basolaterally expressed. However, basolateral sorting based on tyrosine or di-leucine motifs is not affected.

According to this aspect of the invention, inhibitory peptide analogs include any peptides which have the capacity to compete for the cellular mechanisms implemented in basolateral expression of SCF-like proteins, thus leading to abolition or reduction in basoateral expression in a polarized cell.

Any basolateral sorting signal according to the general formula (I) and any peptide or protein comprising this signal are likely, when overexpressed in a polarized cell, to have the capacity to inhibit basolateral expression of a further protein expressed in said cell.

Particularly preferred examples of analog inhibitors include peptides consisting of the heptapeptide basolateral targeting motif of general formula (I), per se, and larger peptides comprising this motif, having for example 8 to 50 amino acids, particularly 8 to 40. It is particularly advantageous to use as inhibitors peptides or proteins which are not themselves basolaterally expressed, but which have sufficient similarity to endogenous basolateral proteins to compete for the same cellular machinery. For example, proteins or peptides comprising the Formula (I) motif, but which do not have transmembrane domains are suitable inhibitors. In general, proteins consisting of, or comprising the cytoplasmic domain defined by Formula (II) above are efficient inhibitors of basolateral expression, particularly for SCF.

A second class of inhibitors according to the invention are inhibitors specifically recognising or interacting with the basolateral sorting signal as described in the present application or specifically recognizing or interacting with the basolateral sorting signal of a peptide or a protein comprising said basolateral sorting signal.

This class of inhibitor is designed to bind to the basolateral or endoplasmic reticulum export determinant with a higher affinity than is required for the determinant to bind to its specific adaptor proteins.

The interaction between the inhibitor and the basolateral sorting signal is specific in that the inhibitor does not significantly cross react with any other intercellular protein. The absence of such significant cross-reactions is shown by the fact that cellular functions other than the basolateral expression of the targeted protein are not disrupted.

Such inhibitors include antibodies (monoclonal or polyclonal), and derivatives of antibodies such as fragments of antibodies or single chain antibodies that recognize the determinants, or intrabodies. An intrabody is a single chain antibody (or single-chain variable region fragments), usually composed of the heavy- and light-chain variable domains in a single polypeptide, and designed for intracellular expression. The antibodies and derivatives can be introduced into the cytoplasm by either membrane permeable complexes or by gene expression in the respective cells induced by gene-therapeutic approaches.

This class of inhibitor also includes peptides, for example peptide aptamers, or synthetic compounds specifically interacting with the two described determinants at high affinity. These inhibitors will be applied to the cell or tissue as described for competitive inhibitors.

A further class of inhibitor acts by disrupting dimerization of wild-type basolaterally expressed proteins. Indeed, gain of function mutations in the cytoplasmic tail of SCF (17H), can be used as an efficient tool to alter or modify the intracellular localization of proteins comprising the basolateral signal such as SCF or CSF-1. Based on the dimerization of SCF and CSF-1 a class of inhibitors can be developed that include the extracellular SCF or CSF-1 domains (required for dimerization) but that carry cytoplasmic determinants that confer transport to lysosomes and subsequent degradation. Such inhibitors require dimerization with the endogenous wildtype proteins in the cells and are generally introduced into the tissue by gene-therapeutic methods. This class of inhibitors includes also peptides or synthetic compounds that specifically bind to the cytoplasmic tail sequences and/or signal as described in formula (I) of endogenous SCF or CSF-1 and carry an additional peptide signal that induces lysosomal targeting of the tagged SCF and CSF-1. Such inhibitors would be applied and consist of the aspects described in the section: competitive inhibitors.

In a further embodiment, the invention relates to screening methods for identifying inhibitors of basolateral expression. The method consists of or comprises the following steps:
   introducing into a polarized cell a compound to be tested for the inhibitory property,
   detecting into said cell modification of basolateral expression of a reporter protein and emergence of apical expression for this reporter protein,
   optionally recovering the test compound seen to have an inhibitory effect on basolateral expression.

The introduction into a cell of the compound to be tested can be achieved by different means. In particular, if the inhibitor to be tested is a peptide, a nucleic acid molecule encoding this peptide can be integrated into a vector and the cell be transformed by the vector. If the inhibitor to be tested is a synthetic compound, it can be introduced by membrane permeation.

By comparison of the apical expression of the reporter protein before and after introduction of the inhibitor to be tested, it can be established whether the potential inhibitor modifies the basolateral targeting, or not.

Preferably, the reporter protein is a chimeric GFP-SCF protein as illustrated in FIG. 1. In this case, it is thus very simple to monitor the fluorescence on the apical membrane. An increase of 20% of the intensity of fluorescence on the apical face after the introduction is representative of a perturbation in basolateral sorting machinery. The screening method is preferably conducted simultaneously with control compounds which are known not to disturb the basolateral sorting machinery of the cell.

The invention also relates to inhibitors of the basolateral targeting signal obtainable by carrying out the screening method according to the preceding description.

Inhibitors identified in this way include peptides, antibodies and derivatives such as a fragment of an antibody, single chain antibodies, intrabodies, peptides expressed as part of a library of random molecules, for example in a phage of a phage library, or synthetic compounds.

The present invention also relates to nucleic acid molecules encoding a peptidic inhibitor as described above and to nucleic acid molecules which are complementary to the preceding nucleic acid molecule.

In a fourth aspect, the present invention relates to different uses of the peptides and proteins consisting of or comprising the basolateral sorting signal according to the invention, as well as uses of the inhibitors described above. The invention also relates to methods exploiting the knowledge of this new basolateral sorting signal.

Firstly, the comparison of the general formula (I) with cytoplasmic tails of membrane proteins can help in predicting whether the expression of the protein will be basolateral. In so far as many sequences are identified whose function are unknown, the identification of a basolateral sorting signal in this sequence can be used to identify the potential function of the protein encoded by the sequence.

For proteins already known to be basolaterally expressed, the identification of the basolateral sorting signal may be essential to the understanding of the function of the molecule. For example, it could allow the determination of which residues are crucial and may explain some loss of function by a single amino acid mutation. Moreover, as discussed above, the basolateral sorting signals have different endocytotic characteristics. Proteins which comprise a basolateral sorting signal according to the invention are likely to have a prolonged exposure at the cell surface, which can give rise to particular properties.

For example, the data on the basolateral sorting signal of the invention has significantly contributed to improving knowledge of CSF-1. Only a limited amount of data is present in the literature about cell surface transport of CSF-1. The inventors are the first to demonstrate a basolateral targeting domain in CSF-1 by comparison with the general formula (I). Besides this determinant, further comparison between the cytoplasmic tail of CSF-1 and SCF reveals an additional conserved C-terminal valine residue.

In a preferred embodiment, the invention relates to use of peptide to modify the general sorting machinery of a cell. A particularly preferred use of the invention is the use of a peptide or protein comprising the basolateral sorting signal to inhibit basolateral expression of a transmembrane protein which is normally specifically expressed in the basolateral membrane of polarized cells. This can be particularly useful for abolishing basolateral sorting of transmembrane proteins bearing a mono-leucine basolateral sorting signal, being of type I or type II topology.

According to the data presented in the experimental section below, a particularly preferred transmembrane protein is SCF. Results showing the diminution of basolateral expression accompanied by an emerging apical expression are given in the experimental section. In this case, the modification of basolateral sorting can be monitored as a function of the level of expression of the peptide or protein designated to disturb the sorting machinery.

In a further embodiment, the invention relates to a method for modulating basolateral expression of a basolaterally targeted transmembrane protein P. This method comprises the introduction into a cell expressing P of a basolateral sorting signal according to the invention or a protein or peptide comprising this signal as described before.

This method is advantageously carried out to modulate basolateral expression of the protein SCF in a polarized cell expressing this protein. This cell can be selected from Sertoli cells, keratinocytes, lung epithelial cells, kidney epithelial cells, endothelial cells of skin, cells from respiratory and alimentary tract, from aorta, from bone marrow, osteoblasts, thymic epithelial cells, ovaries cells, and neurons expressing SCF.

According to the Function B of the signal of the invention, a second method can also be envisaged. This is a method for modulating membrane retention of a transmembrane protein T. This method comprises the introduction into a cell expressing T of a basolateral sorting signal according to the invention or a protein or peptide comprising this signal as described before.

This method is advantageously carried out to modulate membrane retention of the protein SCF in a cell expressing this protein. This cell may be polarized or non-polarized. Examples of polarized cells expressing SCF are given above. If the cell is not polarized, it can be selected from dermal fibroblasts, heart atrium, smooth muscle cells of the aorta, bone marrow stromal cells and Leydig cells.

According to a further aspect of the invention, there is provided a method for obtaining basolateral expression of a transmembrane protein T containing the basolateral sorting signal of general formula (I), said method comprising expressing in a polarized cell a nucleic acid encoding the said protein.

In this method, the transmembrane protein T may be a chimeric protein comprising i) a soluble protein P, ii) a signal peptide, iii) a transmembrane domain and iv) the basolateral signal of the invention. The chimeric nature of the protein arises from the fact that at least one of the signal peptide and the transmembrane domain is heterologous with respect to protein P.

This method can therefore constitute a means of conferring basolateral expression and retention characteristics on the soluble protein P. Such a method may involve the cloning of a nucleic acid encoding a signal peptide, of the nucleic acid sequence encoding protein P, of a nucleic acid encoding a transmembrane domain and of a nucleic acid sequence encoding a basolateral sorting signal according to the invention, in an expression vector, followed by expression of the encoded protein in a polarized cell. The expression vector may be for example a plasmid or a viral vector.

Spacers can be introduced between the different sequences. The different sequences are in the same reading frame. The expression vector comprises all the necessary properties to ensure the expression of the inserted sequences. The induction and the level of expression are characteristics of the chosen vector. They can be adjusted and adapted to the cell in which the chimeric protein is intended to be expressed.

In another variant of this embodiment, basolateral expression characteristics are conferred on a transmembrane protein T. This variant involves the introduction into T of a cytoplasmic tail having the formula

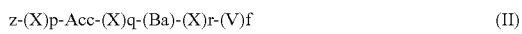

$$z\text{-}(X)p\text{-}Acc\text{-}(X)q\text{-}(Ba)\text{-}(X)r\text{-}(V)f \qquad (II)$$

wherein each X independently represents an amino acid residue; z represents a lysine or an arginine residue; p represents an integer from 12 to 22; q represents 0 or an integer from 1 to 4; r represents an integer from 2 to 12; Acc represents an acidic cluster; Ba represents the basolateral sorting signal according to any one of claims 1 to 5; $(V)_f$ represents a valine, f represents 0 or 1 and wherein the multiple amino acid residues represented by (X) can be the same or different. The cytoplasmic tail of formula (II) is heterologous with respect to the protein T. The introduction of such a cytoplasmic domain into T can be made simultaneously with a total or partial deletion of the amino acid sequence of the endogenous cytoplasmic tail of said transmembrane protein. It is also possible to insert the cytoplasmic tail of general formula (II) into the endogenous cytoplasmic tail without deleting any pre-existing endogenous amino acids. In this case, the insertion of the cytoplasmic tail of formula (II) is preferably made immediately after the transmembrane domain.

According to the present invention, SCF and CSF-1 are examples of proteins carrying the basolateral sorting signal described in the application. In respect of the plurality of cells expressing SCF, uses and methods directed to the modification of the cellular roles of SCF are particularly interesting.

Figure 8:
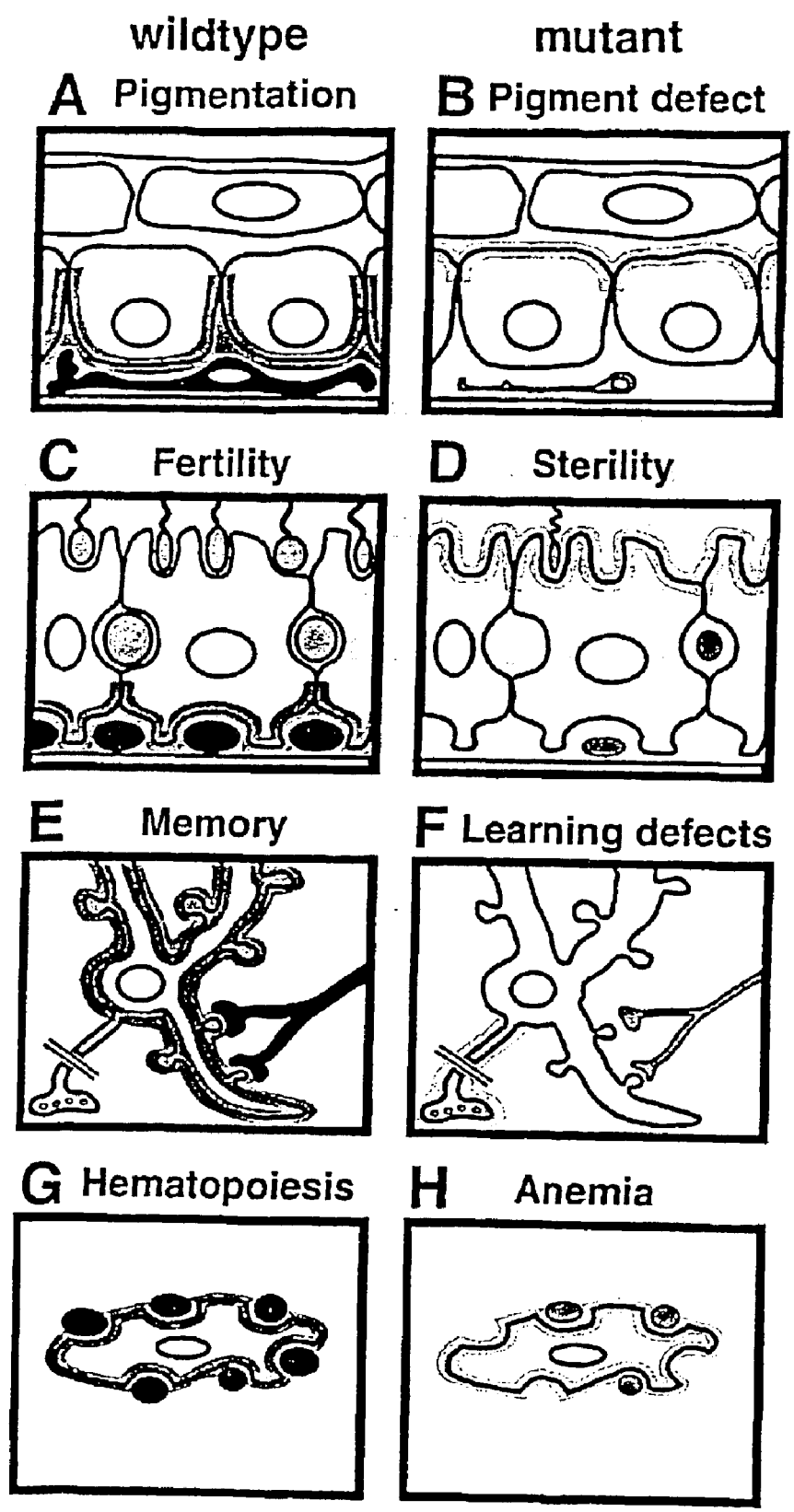

The invention suggests multiple roles for the cytoplasmic tail of SCF. First, SCF is targeted to the cell surface in a polarized fashion, being expressed basolaterally and not at the apical surface. Second, after reaching the surface, SCF is retained at the plasma membrane. The first function of the cytoplasmic tail would be important in cells within polarized tissues, such as keratinocytes, Sertoli cells and neurons, whereas the second function would be relevant to all SCF expressing cells (FIG. 8). Therefore, the absence of basolateral delivery of SCF, leads to the death of melanocytes and male germ cells, which normally require basal delivery of SCF from polarized keratinocytes and Sertoli cells respectively as illustrated by the $Mgf^{S117H}$ mutation (8). In addition to the loss of pigmentation and fertility, the absence of spatial learning has been demonstrated in a mouse mutant of SCF (Mgf$^{Sld}$) which lacks the transmembrane and cytoplasmic domain (4). In contrast to wildtpye SCF, such mutant forms of SCF are secreted from the apical surfaces of polarized epithelia (8). Cell surface expression of SCF in unpolarized stromal cells of the bone marrow is required for hematopoiesis (8). Consequently, constitutive endocytosis resulting in reduced cell surface expression of SCF would lead to a hematopoietic defect comparable to that of the Mgf$^{Sl17H}$ mutant mice (6,7).

Particularly preferred cells are keratinocytes in which the role of SCF has been investigated by the inventors.

The skin is one of the largest organs of our body. It is composed of a vascularized dermis, which supports the stratified epidermis. Within the basal layer of the epidermal keratinocytes, melanocytes are interspersed in regular intervals. In addition to important functions in immuno-surveillance, homeostasis and UV protection, differences in skin pigmentation are also the base for racial conflicts as well as psychological problems associated with irregular pigmentation.

It is not the quality of the pigment (red brown or black), but rather the homeostasis between the number of melanocytes and keratinocytes which is not understood. When this balance is disrupted, local absence or overproliferation of melanocytes can have dramatic psychological as well as pathological consequences. A tool to modify the number as well as the localization of melanocytes in the epidermis is therefore of major cosmetic as well a medical importance.

A tool to modify the number as well as the localization of mast cells is also of major medical importance. Mast cells protect the body from certain parasites. However, they are also the cause of pathogenesis such as asthma and other allergic diseases (notably of the skin). Mast cells do express the tyrosine kinase c-kit and they need the ligand SCF for migration, survival, proliferation and histamine release. Upon stimulation of mast cells by extreme temperature differences, mechanical stimuli or/and occupancy of the IgE (FcRI) receptors they induce inflammatory reactions by secreting histamine and other inflammatory mediators. Blocking the function of mast cells may have beneficial effects on allergic reactions of the skin after sun burn or other skin damaging events. It may also have a beneficial effect against asthma.

In a further embodiment, the invention relates to the use of a composition comprising a protein or peptide comprising a basolateral sorting signal of the invention, and/or a nucleic acid encoding for them, and/or an inhibitor of the invention, for the manufacture of a medicament to modify the intercellular function of SCF, particularly the function of surface expression.

In a preferred embodiment, the invention relates to the use of this composition to modify the role of SCF leading to a decrease of melanocytes proliferation number and change in melanocytes localization. Preferably, the composition is used to reduce hyperpigmentated skin lesions such as lentigo, lentigo senilis or nevi.

In another preferred cases, the composition is used to eliminate melanocytes from UV damaged skin. It can also be used to treat melanoma cells.

According to the role of SCF in hematopoiesis and in mast cells proliferation, the composition can be used to prevent allergic reactions mediated by mastocytes in the airway and alimentary tract, to treat monocytosis, leukaemia or mastocytomas. This composition may also advantageously be administered treat hematopoietic precursor cell neoplasma, e.g. acute lymphoblastic leukemia (ALL).

According to the role of SCF in male and female germ cells, the composition can be used to treat inhibition of spermatogenesis or oogenesis or to block spermatogenesis or oogonesis.

The posology as well as the way of administration are to be determined by the clinic expert. When the defect causing the pathology to be treated is genetic, gene therapy would be very advantageously envisaged.

According to the involvement of SCF in skin pigmentation, a composition comprising a protein or peptide comprising the basolateral sorting signal of the invention can be used in dermatology for cosmetic purposes. The protein or peptide comprised in the composition may be replaced or completed by a nucleic acid coding for them, and by an inhibitor according to the invention. For uses in cosmetology, the composition is preferably administered by a topical application. For this type of application, the composition is preferably in the form of a cream, a spray, a lotion, an ointment or a powder and is applied directly on the skin.

As outlined in the description, the structural and functional homologies between CSF-1 (CSF-1; macrophage colony stimulation factor) and SCF are substantial. Similar to SCF, CSF-1 is produced as a membrane-bound growth factor that is subsequently released from the cell surface by proteolytic cleavage at membrane proximal sites. Therefore the transport of CSF-1 to the cell surface, as it is the case for SCF, is crucial to obtain biological activity. The biological consequences for altered CSF-1 expression are well defined in respect to pathological situations, like Alzheimer disease, various chronic inflammatory diseases (arthritis, rheumatism, psoriasis) that are due to aberrant recruitment of macrophages to the lesioned site.

An additional obvious function of CSF-1 concerns the formation of osteoclasts from circulating macrophages. Osteoclasts are relevant for diseases that involve loss of bone tissue, such as osteoporosis. All these pathological situations depend on the recruitment and local proliferation of macrophages by enhanced expression of CSF-1. Reducing the surface levels of CSF-1 may therefore be an effective way to reduce tissue damage or bone removal induced by recruitment of macrophages.

In another embodiment, the invention relates to the use of a composition comprising a protein or peptide comprising a basolateral sorting signal of the invention, and/or a nucleic acid encoding for them, and/or an inhibitor of the invention, for the manufacture of a medicament to modify the roles of CSF-1.

According to this, this composition can be used to treat abnormal immune response, in particular to treat psoriasis or artherosklerosis.

In another embodiment of the invention, the composition can be used to treat osteoporosis or hyperparathyroid bone.

Clearly defined targeting determinants in SCF and other transmembrane growth factors offers possibilities for altering polarized presentation and cell surface expression of these factors. This gives rise to new therapeutic approaches for treatment of pathological conditions, such as allergies, chronic inflammation, osteoporosis or hyper-pigmented lesions, caused by overexpression or mutations of these factors.

Various aspects of the invention are illustrated in the figures:

FIG. 1. SCF-GFP chimeras localize to the basolateral aspect of polarized MDCK II cells.

Confocal microscopy of wildtype membrane bound (M2) SCF-GFP proteins (A, FITC channel) and anti-E-cadherin staining (B, Texas Red channel) of fixed MDCK II. A corresponding Z-scan of the monolayer is shown below. Note the overlap of staining in lateral regions of individual cells.

Above the panel, a schematic view of the two differentially spliced wildtype forms of SCF (SCF-M1, cleavable and SCF-M2, noncleavable) and the chimera of SCF with GFP (SCF-GFP) is shown. EGFP was inserted 5' to the exon 5/6 junction (SSTLGPEK/DSRV) (SEQ ID NO: 77) which resulted in the following sequence: SSTLGP EQKLISEEDLGQS-IV . . . (EGFP) . . . YK-TGPEK/DSRV (SEQ ID NOS: 22 and 23) (single letter amino acid code; the sequence of the myc tag is underlined). SP, signal peptide; RBD, SCF receptor binding domain; PCS (arrow), proteolytic cleavage site; MD, membrane domain; CT cytoplasmic tail; EGFP, enhanced green fluorescent protein (the myc epitope tag is omitted from the drawing for clarity). The bar in B corresponds to 24 µm.

FIG. 2. Cytoplasmic tail sequences of wildtype and mutant SCF.

(A) Alignment of sequences of wildtype and cytoplasmic tail mutants of mouse SCF and their respective steady state distribution in MDCK II cells (SEQ ID NOS: 33–60). (1) The name of the constructs represents the site of amino acid deletions (marked with a dotted line) or point mutations (bold and underlined). (2) Steady state localization of GFP and Tac SCF chimeric proteins in polarized MDCK II cells (wt, wildtype; BL, basolateral; AP, apical). Deletions are marked with a dotted line and point mutations are bold and underlined. (3) Steady state distribution; S, surface; I, internal on ER (ER) or vesicular (vesic). (4) The ability to endocytose has been indicated for each of the constructs (−, not internalized; +, moderately internalized; ++, strongly internalized; +++, very strongly internalized; nd, not determined).

(B) Clustal W alignment of different SCF transmembrane domain and cytoplasmic tail sequences (SEQ ID NOS: 61–72). GenBank accession numbers: human (M59964), mouse (M57647), dog (S53329), horse (AF053498), cow (D28934), sheep (U89874), cat (D50833), swine (L07786), chicken (D13516), quail (U43078) and *Ambystoma mexicanum salamander* (AF119044). The sequence for rattus norvegicus (rat, AF071204) is identical to mouse.

Figure 3:
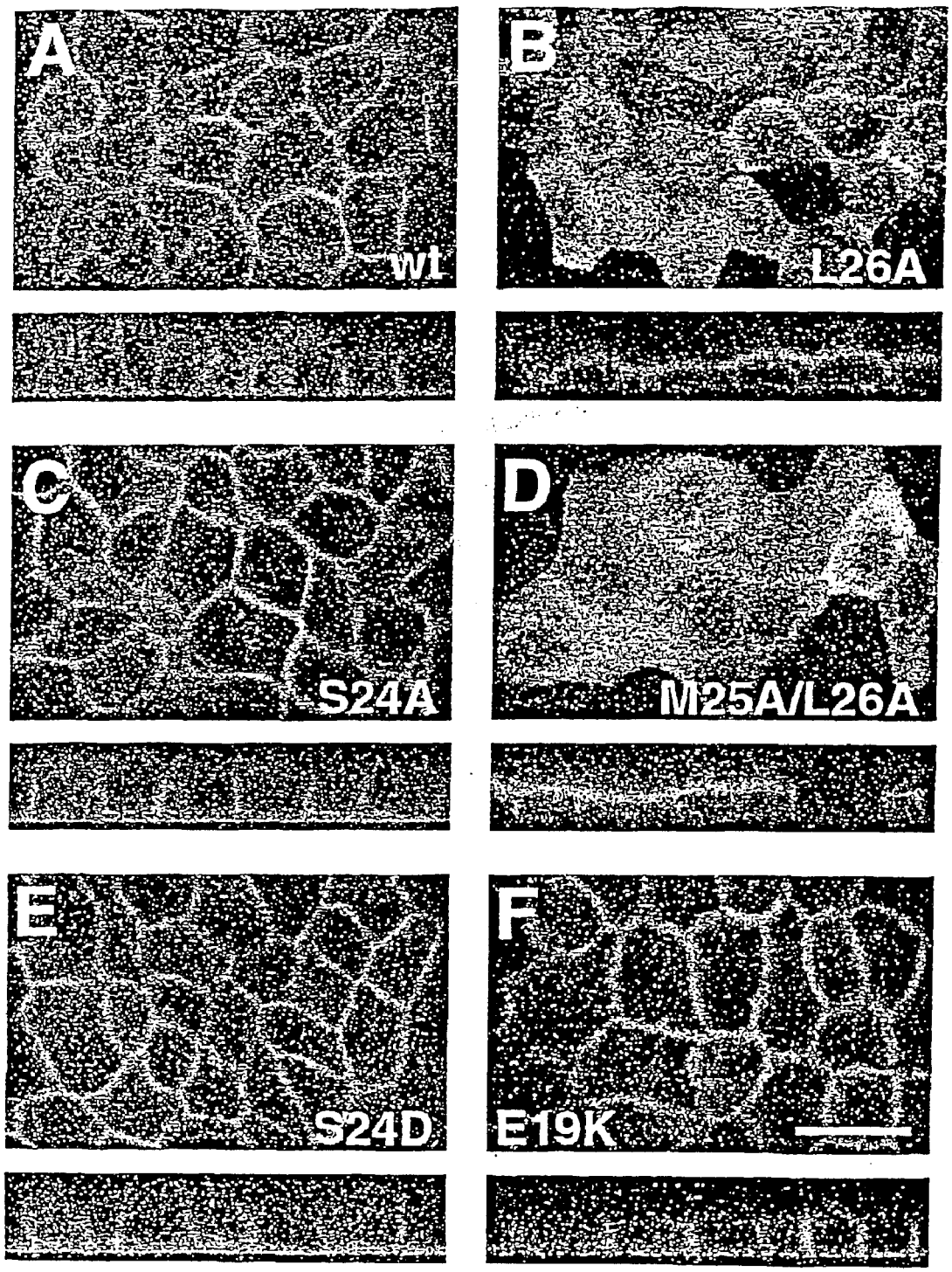

FIG. 3. Leucine 26 is required for basolateral targeting of SCF-GFP constructs in polarized MDCK II cells.

Confocal microscopy (FITC channel) of live wildtype (A) and mutant SCF-GFP-M2 (B-F) expressing confluent MDCK II cells. Basolateral staining is lost upon mutation of leucine 26 to alanine (B), or methionine 25 and leucine 26 to a double-alanine (D). Replacement of serine 24 to alanine (C) or aspartic acid (E), as well as the change of glutamic acid 19 to lysine (F) did not alter basolateral localization of the constructs. Below each panel a corresponding Z-scan is shown. The bar in F corresponds to 24 µm.

FIG. 4. The basolateral targeting determinant in SCF acts independently of the extracellular domain.

Confocal microscopy of anti-Tac antibody stained fixed MDCK II cells stable transfected with Tac-EGFP (A) and wildtype (B) or mutant (C-F) Tac-SCF chimeric constructs. A scheme representing the Tac-SCF chimera is shown above the panel. The fusion protein consists of the extracellular domain of the IL2 receptor alpha chain (Tac) and the transmembrane and cytoplasmic sequence of SCF. Unmodified Tac with C-terminal EGFP fusion of which the anti-Tac antibody staining is shown (A). Tac-SCF chimera with wildtype SCF sequences (B). Deletion of the last 8 amino acids from the cytoplasmic tail of SCF does not alter basolateral targeting of the Tac hybrid (d29) (C). However, removal of the last 15 amino acids (d22) (D), or amino acids 21-28 (E) resulted in an apical localization of Tac-SCF. The deletion of amino acids N-terminal to the leucine 26 containing region (d12-20) resulted in basolateral as well as apical localization of the chimeric proteins (F). Below each panel, a corresponding Z-scan is shown. SP, signal peptide of SCF and Tac respectively; ED, extracellular domain. The bar in F corresponds to 24 µm.

Figure 5:
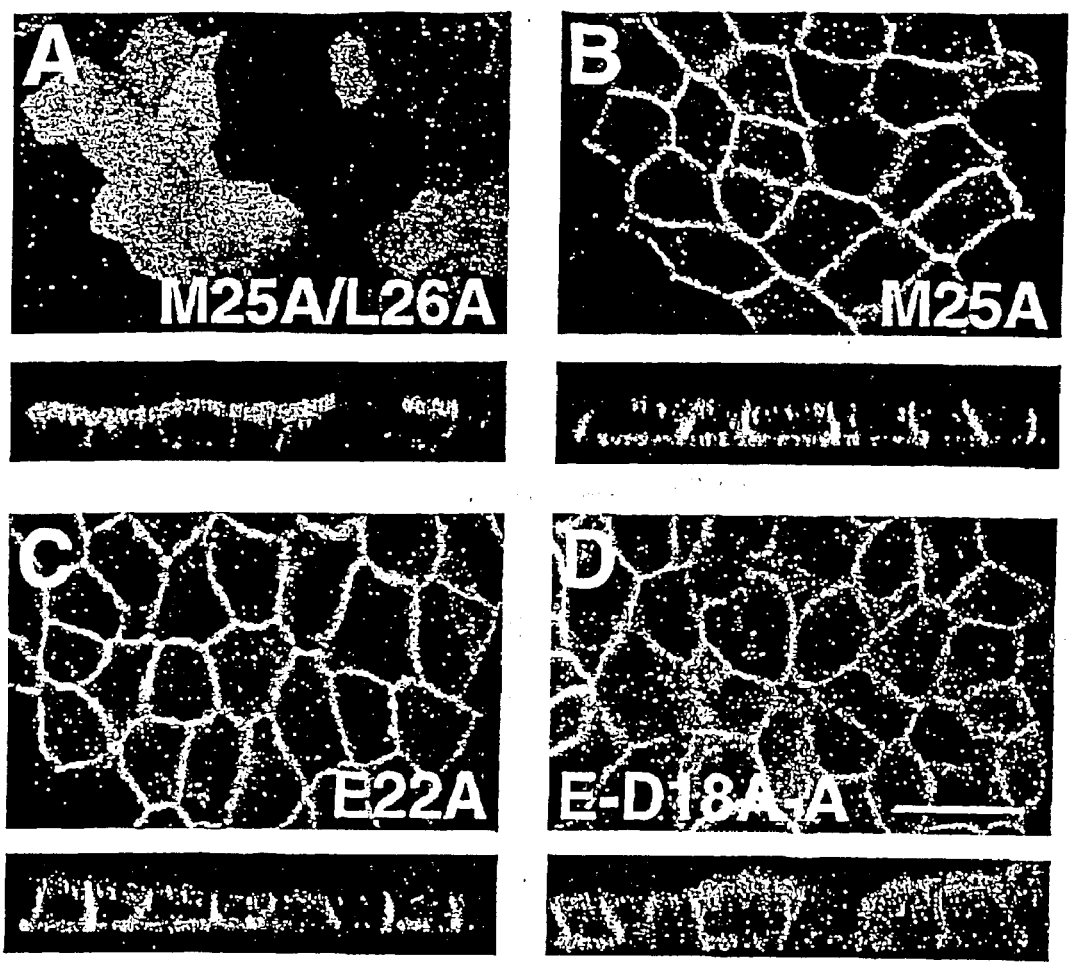

FIG. 5. An acidic cluster assisted monomeric leucine dependent basolateral targeting determinant Confocal microscopy of anti-Tac antibody stained fixed MDCK II cells stable transfected with Tac-SCF point mutations of hydrophobic and acidic amino acids. Apical localization of the Tac-SCF chimera carrying a double alanine substitution of methionine 25 and leucine 26 (M25A/L26A) (A). The single point mutation at methionine 25 to alanine did not alter basolateral targeting (B). Similarly, the point mutation of glutamic acid 22 to alanine (E22A) did not influence basolateral targeting (C). Alanine substitution of the acidic cluster $^{18}$EED$^{20}$ (E-D18A-A) resulted in basolateral as well as apical accumulation of Tac chimeric proteins (D). Below each panel, a corresponding Z-scan is shown. The bar in D corresponds to 24 µm.

Figure 6:
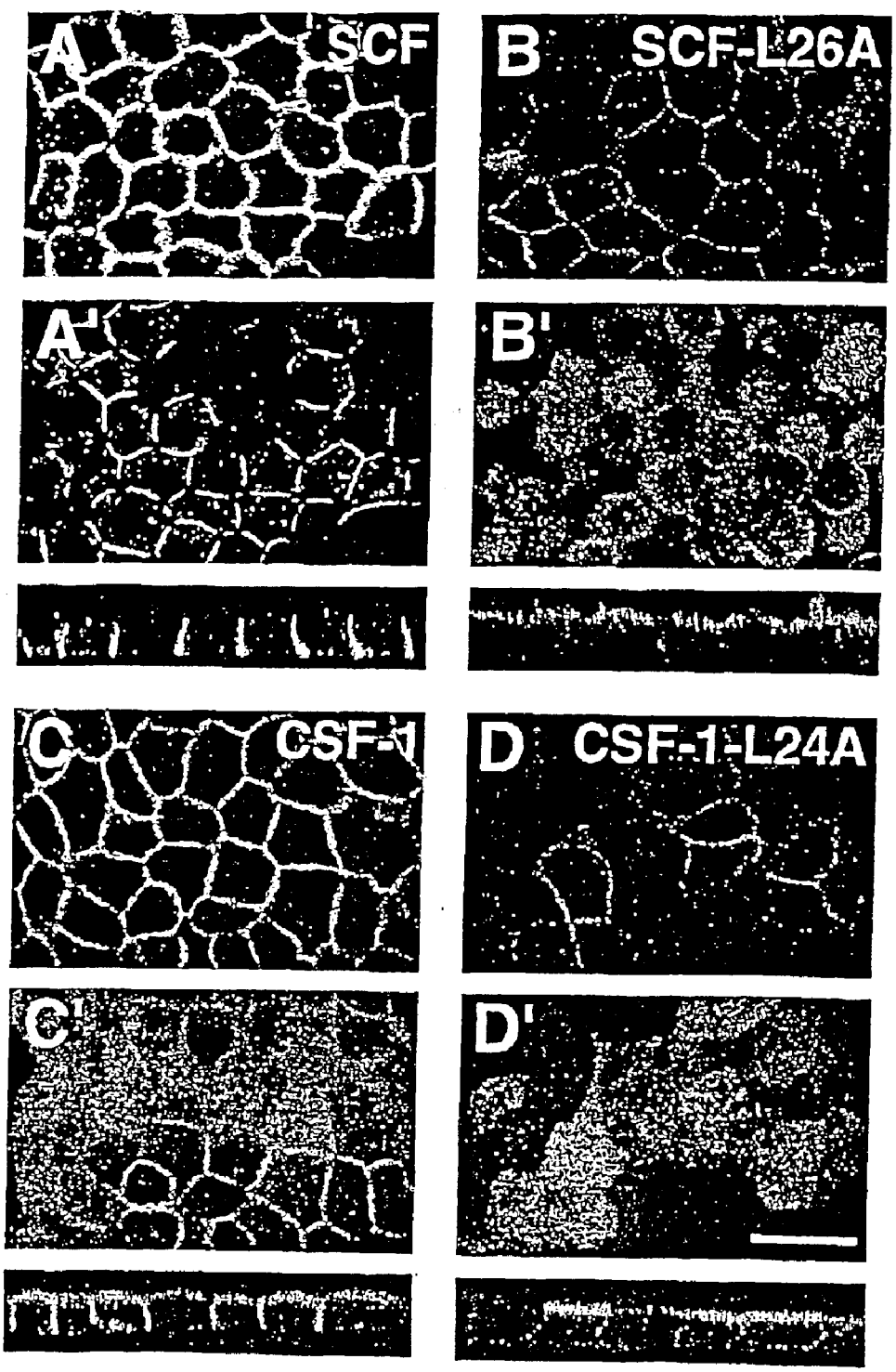

FIG. 6. Functional conservation of the leucine determinant in CSF-1

Confocal microscopy of anti-Tac antibody stained, fixed MDCK II cells stably transfected with wildtype and leucine to alanine (L26A, SCF; L24A, CSF-1) mutation of Tac-SCF (A, B) and Tac-CSF-1 (C, D) chimeras. A confocal section at the level of the nucleus (A, B, C, D) and the apical cell surface (A', B', C', D') is shown to appreciate the differences between basolateral and apical expression of wildtype versus mutant chimeric constructs at steady state levels. Below each panel, a corresponding Z-scan is shown. The bar in D' corresponds to 24 µm. (E) Comparison of the cytoplasmic tail sequences of mouse SCF (SEQ ID NO: 73) with mouse CSF-1 ( SEQ ID NO: 74). The basolateral targeting sequences for SCF, identified in this study (acidic cluster and leucine$^{26}$) and the functionally conserved leucine$^{24}$ in CSF-1 are underlined.

Figure 7:
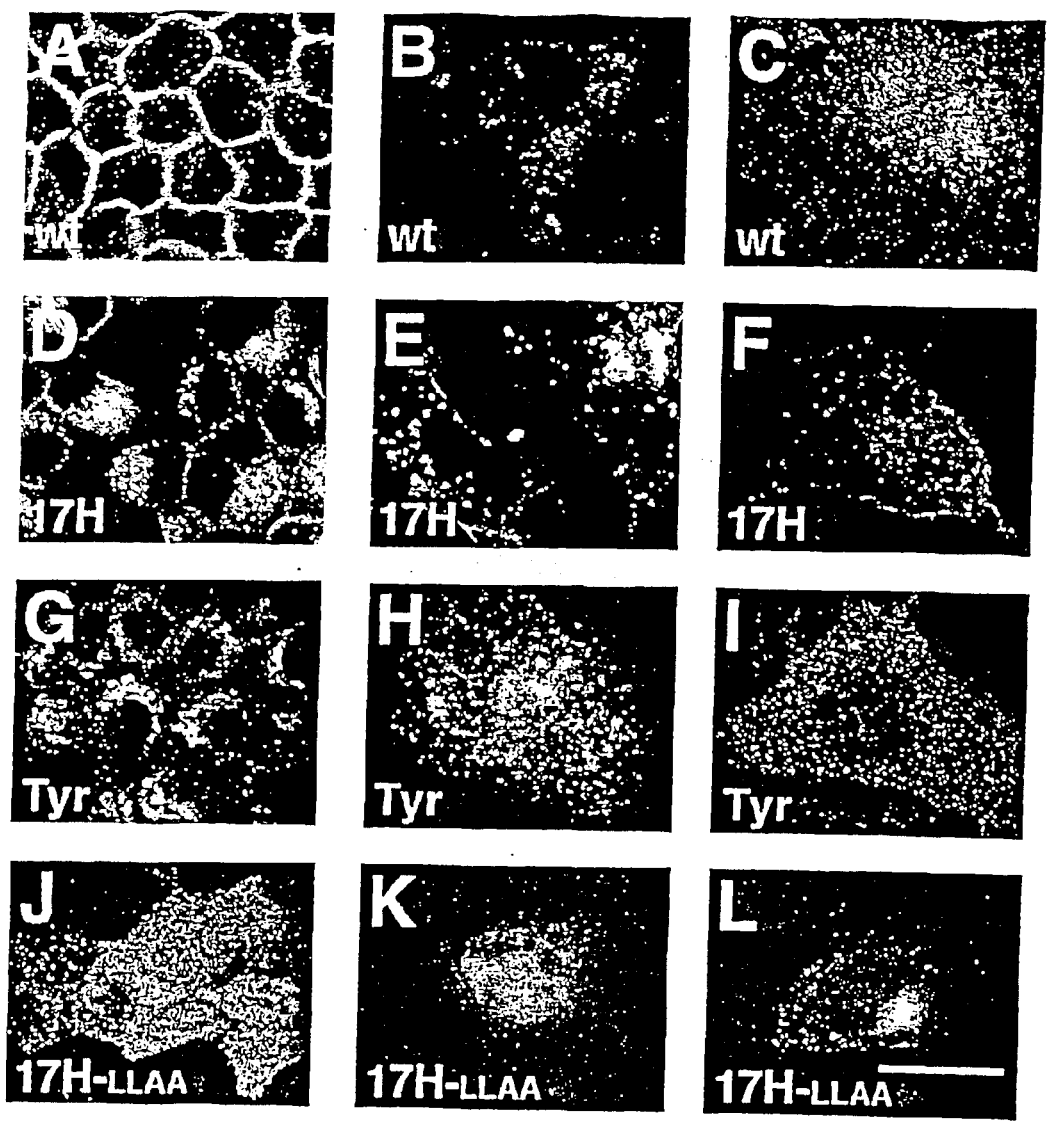

FIG. 7. Endocytosis of Mgf$^{Sl17H}$ mutant Tac-SCF by a lysosomal targeting signal.

Confocal microscopic sections at the level of the nucleus or apical surface of anti-Tac antibody labeled confluent MDCK II stable transfected with different Tac-SCF constructs (A, D, J) and Tac-tyrosinase (Tac-tyr, G). Only a weak staining of intracellular Tac chimeras is detected in wildtype Tac-SCF expressing cells (A). In cells transfected with the Tac-SCF-17H (D) construct, extensive intracellular vesicular anti-Tac staining can be observed, which resembled cells transfected with the Tac-tyr chimera (G). Mutation of the di-leucine of the putative internalization motif of Tac-SCF-17H to a di-alanine (17H-LLAA) resulted in a loss of intracellular but led to apical localization (J).

Standard fluorescence microscopy of endocytosed anti-Tac antibody bound to wildtype and mutant Tac-SCF or Tac-tyr constructs transiently transfected into COS-7 cells. After 30 minutes at 37° C., internalized Tac-SCF (or tyr)/ anti-Tac antibodies complexes were visualized with (B, E, H, K) or without (C, F, I, L) acid removal of cell surface bound non-internalized antibodies. Wildtype Tac-SCF proteins were not internalized during the 30 minute incubation period (B). In contrast, Tac-SCF-17H mutant proteins accumulated in large intracellular vesicles (E). Likewise, Tac-tyr constructs were efficiently internalized (H). However, the di-leucine mutation in Tac-SCF-17H (17H-LLAA) abolished the capacity to internalize cell surface bound anti-Tac antibodies (K). Comparable levels of the different Tac-SCF constructs were initially expressed on the COS-7 cell surfaces as illustrated by staining of parallel cultures from which the anti-Tac antibody was not removed from the cell surface (C, F, I, L). The bar in L corresponds to 24 μm.

FIG. 8. Multiple biological effects of cytoplasmic mutations in SCF.

Illustration of the polarized expression of SCF in basolateral and dendritic aspects of basal keratinocytes (A), Sertoli cells (C) and neurons (E) respectively. Cell surface expression of SCF is also found in non-polarized stromal cells of the bone marrow or dermal fibroblasts in the skin (G). Cell surface SCF protein is represented by gray shading and c-kit expressing (SCF dependent) cells by dark shading (A, C, E, G). The mutation of the cytoplasmic targeting determinants of SCF leads to apical or axonal accumulation as well as reduced cell surface expression (light shading in B, D, F, H). Consequently, pigmentation defects (B), sterility in males (D), learning (F) and hematopoietic defects are observed in the respective tissues (H) (affected cells are indicated by reduced size, numbers and gray shading; B, D, F, H). Note, dendritic and axonal localization of wildtype and cytoplasmic mutant SCF protein in neurons is extrapolated from the polarized expression patterns in epithelial cells reported in this paper. The loss of spatial learning has so far only been demonstrated in mice lacking transmembrane and cytoplasmic sequences of SCF ($Mgf^{Sld}$) (4), a mutant form of SCF which is secreted from apical aspects of polarized epithelia (8). wt, wildtype tissue; mutant, tissue expressing cytoplasmic tail mutants of SCF.

Figure 9:
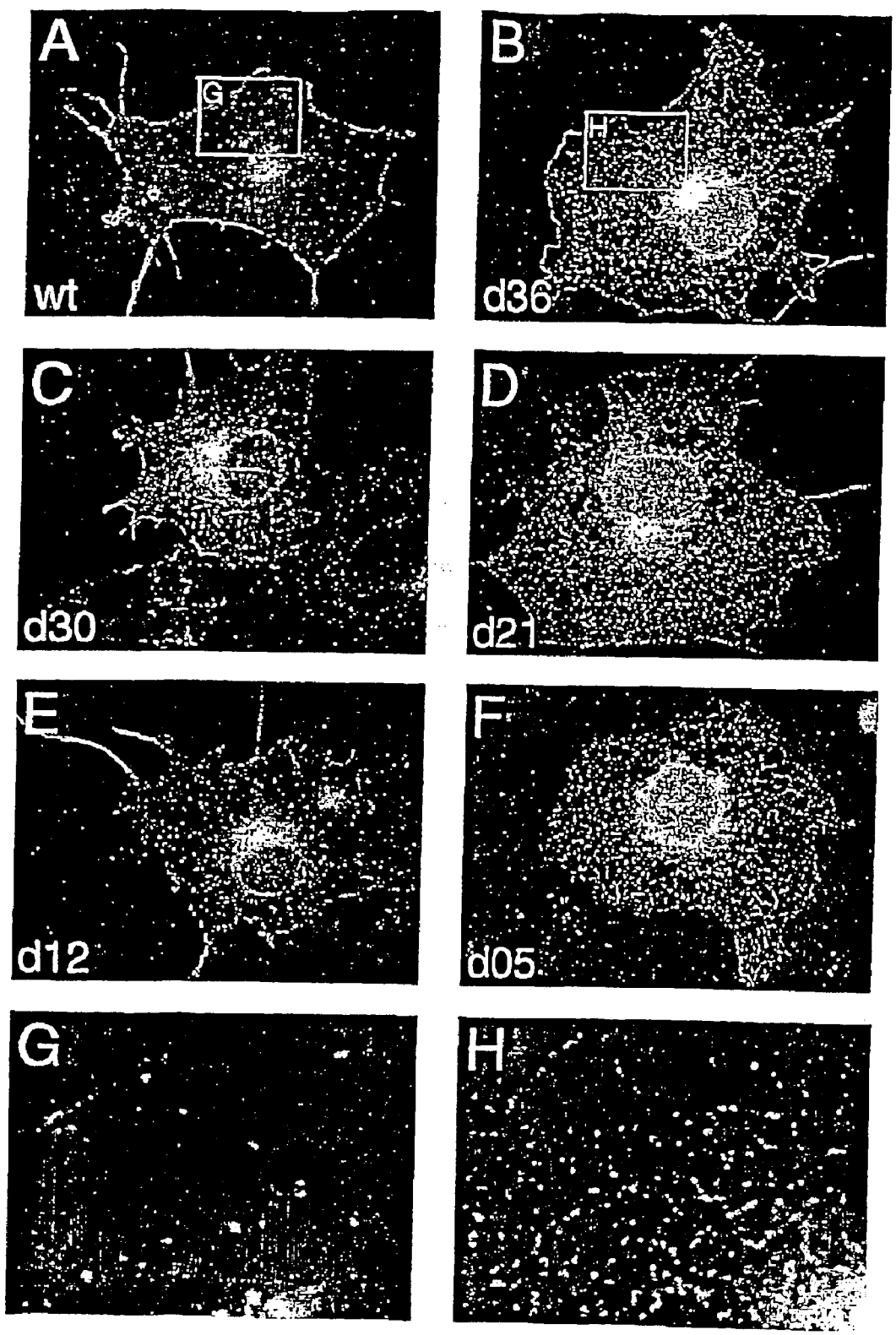

FIG. 9: Accumulation of SCP-GFP proteins in the ER compartment

Cos-7 cells have been transiently transfected with wildtype or C-terminally deleted SCF-GFP fusion proteins. After 24 hours, GFP fluorescence was recorded. Panel G and H represent magnified views of the indicated areas in A and B. wt, wildtype cytoplasmic tail; d36-d05, C-terminal deletions corresponding to the amino acids of the cytoplasmic tail of SCF.

FIG. 10

A: Model of SCF including the two targeting domain and the putative adaptor proteins.

B: Possible model how the localization and behavior of melanocytes in the epidermis could be modified by altering basolateral exppression of SCF (middle panel) or reduced cell surface expression (right panel).

FIG. 11

Monolayer of MDCK II cells double transfected with GFP-SCF-CT and Tac-SCF reporter. The GFP fluorescence is shown in A and the anti-Tac antibody staining (revealed with Texas-red in B). The Tac-SCF staining is disrupted in the highly positive GFP-SCF-CT cell.

FIG. 12:

Confocal section of a MDCK II monolayer transfected with GFP-SCF-CT and Tac-SCF reporter. The anti-Tac antibody staining of the monolayer is shown in A, while the GFP-SCF-CT fluorescence is shown in B. Below each panel the corresponding Z-scan (along the indicated white line) is shown. The Tac-SCF reporter accumulates apically in high expressing GFP-SCF-CT cells.

EXAMPLES

In the following examples, the Experimental Procedures are presented in Examples 1 to 3 and the results are presented in Example 4. Example 5 relates to further mutations. Examples 6 and 7 present data concerning the role of the C-terminal valine and inhibition of basolateral expression by the cytoplasmic tail, respectively.

Example 1

SCF Chimeras and Site Directed Mutagenesis cDNA for SCF and Tac were kindly provided by Drs John Flanagan (Boston) and Pierre Cosson (Geneva) respectively. Mouse CSF-1 and mouse tyrosinase cDNAs were kindly provided by Drs Willy Hostetter (Bern) and Friedrich Beermann (Lausanne) respectively. SCF-GFP chimeras were constructed in pcDNA3 (Invitrogen) by inserting the enhanced GFP sequence (Clontech) together with a myc-tag 5' to the exon 5/6 junction of SCF (SSTLGPEK/DSRV) (SEQ ID NO: 77) which resulted in the following sequence: SSTLGPEQKLISEEDLGQS-IV . . . (enhanced GFP) . . . YK-TGPEK/DSRV (SEQ ID NOS: 22 and 23) (single letter amino acid code; the sequence of the myc-tag is underlined). In order to prevent translation at internal start sites producing cytoplasmic GFP, the start codon of GFP was replaced with nucleotides coding for a ClaI site. A unique PinAI site was introduced C-terminal to the GFP sequence in order to swap wildtype and mutant cytoplasmic tail sequences at this site.

To generate the Tac-SCF chimera (all in pcDNA3), the transmembrane and cytoplasmic domains of SCF were swapped at a unique BglII site in Tac located at a homologous leucine (L) and glutamine (Q) residue upstream of the transmembrane sequences of SCF and Tac. This resulted in the sequence: . . . SIFTTDLQWTAMALP . . . (SEQ ID NO: 24) at this position (conserved LQ is bold and transmembrane residues of SCF are underlined).

The Tac-CSF-1 and Tac-tyrosinase (Tac-tyr) chimeras were constructed in a similar way. CSF-1 and tyrosinase transmembrane and cytoplasmic sequences were PCR amplified with a Bgl II site containing forward primer: (CSF-1: AACAGATCTCCAGATCCCTGAGTCTG; tyrosinase: AACAGATCTCCAAGCCAGTCGTATCTGG) (SEQ ID NOS: 25 and 26) at a common glutamine residue (Q) and swapped with the Tac sequence of this region creating the respective junctional sequences. Tac-CSF-1: . . . SIFTDL-QIPESVFHLLV . . . (SEQ ID NO: 27) and Tac-tyr: . . . SIFTTDLQASRIWPWLL . . . (SEQ ID NO: 76) (the common glutamine residue (Q) is bold and the respective transmembrane region is underlined). Tac-EGFP was cloned by PCR amplification of EGFP with a HindIII containing primer and inserted at a unique HindIII site at the extreme C-terminus of Tac (TIQASSstop) (SEQ ID NO: 78) resulting in the new junctional sequence (TIQASTMV . . . (egfp)) (SEQ ID NO: 28).

Site specific mutagenesis of the cytoplasmic tail of SCF was performed using PCR overlap extension. Two overlapping PCR fragments containing a specific mutation were amplified with external primers (containing either the PinAI or BglII site for SCF-GFP or Tac-SCF chimeras respectively) and swapped with the wildtype sequence of the cytoplasmic tail. All constructs were verified by dideoxy sequencing.

Example 2

Cell Culture, Live Fluorescence Microscopy and Immunocytochemistry

MDCK II cells were kindly provided by Dr. Karl Matter (Geneva) and cultured in DME medium (Life Technologies) supplemented with 10% FCS (Inotech). Cells at 60% confluency were transfected using Calcium-Phosphate as described according to standard protocols and stable clones were selected with 0.6 mg ml$^{-1}$ G418 (Life Technologies). For each construct, at least two different clones were analysed for the steady state distribution of SCF-GFP fluorescence or anti-Tac immunohistochemistry. To visualize the GFP fluorescence, cells were grown to confluency on glass coverslips. Prior to observation, the culture medium was exchanged with F12 medium (Life Technologies) supplemented with 10% FCS, to reduce autofluorescence which is higher in the DME medium. Cells were mounted on an inverted confocal microscope (LSM-410, Zeiss) and visualized with standard FITC optics. In order to reveal the localization of transfected Tac-SCF chimeras or endogenous E-cadherin in SCF-GFP transfected MDCK II cells, monolayers of stable transfected clones grown on glass coverslips were fixed with 4% paraformaldehyde in PBS for 5 minutes. Cells were washed with PBS, permeabilized with 1% Triton X-100 (Sigma) in PBS and blocked with 1% BSA (Sigma) in PBS. Cells were then stained as indicated with either anti-Tac monoclonal antibody 7G7 or with anti Arc-1 monoclonal antibody which is directed against canine E-cadherin. After washing, bound antibodies were revealed with Texas Red coupled anti-mouse antibodies. Fluorescence was subsequently analyzed on a confocal microscope as indicated above. Contrast enhancement was performed in Photoshop (Adobe).

Example 3

Endocytosis Assay

Wildtype and mutant Tac-SCF constructs were transfected into SV40 transformed African Green monkey kidney cells (COS-7) using Fugen 6 according to the manufacturer's recommendation (Roche). 2 days after transfection, cells were cooled on ice and anti-Tac antibodies were added for 1 hour at 1 μg ml$^{-1}$. Prior to warming, unbound antibodies were washed away and internalization was allowed for 30 minutes at 37° C. in DME medium supplemented with 10% FCS. Antibodies which remained cell surface bound were subsequently removed with ice cold acidic glycine buffer (0.1 M, pH 2.5). Cells were then fixed with 4% paraformaldehyde for 5 minutes, washed, permeabilized, blocked and stained with Texas-Red conjugated anti-mouse antibodies (Southern Biotech) to reveal internalized anti-Tac/Tac-SCF complexes (see above). Cells were viewed on an Axiovert 100 microscope (Zeiss), equipped with a digital camera (C4742-95, Hamamatsu) and the Openlab software (Improvision). Contrast enhancement was done in Photoshop (Adobe). The experiment was performed three times with qualitatively similar results and representative examples of cells from one experiment were chosen.

Example 4

Results of Examples 1 to 3 i) Leucine 26 is Required for Basolateral Targeting of SCF.

In order to identify, critical targeting determinants in the cytoplasmic tail of SCF, a green fluorescent protein was created (GFP) containing reporter construct to monitor SCF localization. GFP was inserted into the alternatively spliced extracellular domains of both membrane bound variants of SCF and transfected into polarized epithelial MDCK II cells (FIG. 1). Confocal microscopy revealed that both wildtype constructs accumulated in basal and lateral membranes where they colocalized with E-cadherin, a marker for the lateral membrane compartment in polarized epithelial cells (shown for M2 variant; FIG. 1).

Examination of the wildtype cytoplasmic domain of SCF for the presence of basolateral and intracellular targeting motifs (16) revealed an acidic cluster flanked by a serine at position 24 which matches a recently identified trans-Golgi network (TGN) targeting sequence (19). The phosphorylation of the serine controls the binding of this sequence to the PACS family of adapter proteins. In addition, a methionine-leucine (ML) at position 25 and 26 resembles a signal for endocytosis as well as basolateral sorting from the invariant chain (Ii) of the MHC class II complex (11, 17).

In order to identify the motif in the cytoplasmic tail of SCF responsible for basolateral sorting, various cytoplasmic SCF mutants of the membrane bound (M2) form of GFP tagged SCF (SCF-GFP) were created (FIG. 2A). Mutants lacking the last eight C-terminal amino acids (d36, d29) still localized to the basolateral membrane. However, when 15 or more amino acids were deleted (d22, d12), SCF-GFP was located on the apical membrane, and showed no basolateral expression. The critical region for basolateral sorting was demonstrated to reside within the sequence $^{21}$NEISMLQQ$^{28}$ (SEQ ID NO: 29), since an internal deletion mutant (d21-28) also localized to the apical membrane. Interestingly, in order to be functional, it appeared that this sequence has to be considerably separated from the membrane: deletion of intervening amino acids proximal to the membrane (d5-20) interfered with basolateral sorting. Increasing the distance of the $^{21}$NEISMLQQ$^{28}$ (SEQ ID NO: 29) motif from the membrane by reinserting amino acids 5–11 (d12-20) only partially rescued basolateral targeting, suggesting that other amino acids important for basolateral targeting are present N-terminal to the $^{21}$NEISMLQQ$^{28}$ (SEQ ID NO: 29) motif (see below).

Sequence comparison between human, mouse, chicken and salamander SCF (24) revealed the residues $^{24}$SML$^{26}$ as being completely conserved within the $^{21}$NEISMLQQ$^{28}$ (SEQ ID NO: 29) motif (FIG. 2B). This sequence encompasses a serine at position 24 as well as a di-hydrophobic methionine-leucine at positions 25 and 26 respectively (see above). In order to test whether a portion of this motif was required for basolateral sorting of SCF, we created various point mutations, encompassing these conserved residues (FIG. 2B; FIG. 3). The modification of serine 24 to either an alanine (S24A) or to an aspartic acid (S24D) resembling a phospho-serine, as well as the substitution of the conserved glutamic acid 19 with lysine (E19K) had no effect on basolateral targeting (FIGS. 3C, E, F). In contrast, the modification of leucine 26 to either alanine (L26A) or the replacement of methionine 25 and leucine 26 by a double-alanine (M25A/L26A) led to apical accumulation of the mutant SCF-GFP constructs (FIGS. 3B, D). The analysis of the SCF-GFP chimeric mutant proteins thus suggests that the leucine at position 26 of the cytoplasmic tail of SCF is critical for basolateral sorting of SCF. However, it is not known whether this putative basolateral signal requires the context of dimerized SCF molecules or whether it can provide intracellular targeting information independently.

ii) Extracellular SCF Sequences Are Not Required for Basolateral Targeting.

Dimer formation involving the extracellular domain of SCF or lateral association of the extracellular and/or intracellular portions of SCF with other proteins which contain targeting information may in fact be responsible for the polarized expression of SCF. Therefore, in order to test the ability of the cytoplasmic targeting sequence of SCF to mediate polarized expression independently of the extracellular domain, the latter was replaced with the extracellular domain of the Interleukin-2 receptor alpha chain (Tac) (FIG. 4). Wildtype Tac as well as Tac with a C-terminally fused EGFP accumulated apically when expressed in MDCK II cells (FIG. 4A). In contrast, Tac-SCF chimeras expressing the wildtype cytoplasmic domain of SCF localized to basolateral membranes in a manner identical to the SCF-GFP wildtype constructs (FIG. 4B). Likewise, constructs involving extracellular Tac with deletion mutations of the cytoplasmic tail of SCF (d29, basolateral, FIG. 4C; d22, apical, FIG. 4D; d21-28, apical, FIG. 4E; d5-20, apical (not shown) and d12-20, basolateral/apical, FIG. 4F), showed identical basolateral sorting behaviors when compared to the mutant SCF-GFP constructs. This indicates that the extracellular domain of SCF is not required for basolateral targeting and that the basolateral targeting motif of SCF contained within its cytoplasmic portion is sufficient to direct the Tac extracellular domain basolaterally. Moreover, sequences N-terminal to methionine 25 and leucine 26 removed in the d12-20 mutation influence the efficiency of basolateral targeting (FIG. 4F).

Based on these results, the applicant proposes the existence of a leucine based basolateral targeting signal in SCF. In the absence of this signal, as illustrated by the Sl$^{17H}$ mutation, there is a lack of basal delivery of SCF in keratinocytes and Sertoli cells leading to the death of basal melanocytes and male germ cells respectively (5, 8).

iii) Efficient Basolateral Targeting is Mediated by an Acidic Cluster N-Terminal to the Monomeric Leucine Determinant Although it is evident that the leucine residue at position 26 is critical for basolateral targeting it is not known whether a second hydrophobic residue (methionine 25) as found in all di-leucine like determinants is equally required for basolateral sorting of SCF. Moreover, the region N-terminal to the ML motif that is also required for efficient basolateral targeting ($^{12}$ENIQINEED$^{20}$) (SEQ ID NO: 30) bears a domain important for SCF sorting as well.

To address the first question, methionine 25 was replaced with an alanine residue and the distribution of the Tac-SCF construct was analysed at steady state conditions. In contrast to the leucine 26 to alanine mutation, the change of methionine 25 to alanine did not affect basolateral targeting of Tac-SCF (FIGS. 5A, B). Moreover, replacement of methionine by leucine in an attempt to create a classical di-leucine determinant led to intracellular and apical localization of Tac-SCF (not shown). Therefore, this finding revealed the existence of a novel type of leucine-based basolateral targeting signal in SCF, which does not require a second hydrophobic amino acid in order to be functional.

Analysis of sequences N-terminal to leucine 26 that are absent in the d12-20 mutation, reveal an unusually high concentration of acidic amino acids. An acidic cluster N-terminal to an FI motif has recently been identified as a basolateral targeting signal in the furin protease (25). In order to test whether the acidic cluster in SCF contributes to basolateral sorting or whether other acidic amino acid residues localized closely to the leucine residue are critical, glutamic acid 22 was mutated ($^{22}$ExxxML$^{26}$) (SEQ ID NO: 31) to alanine (SEQ ID NO: 32) (FIG. 5C). In addition, glutamic acid 19 was replaced with a lysine to destroy the acidic cluster formed by residues $^{18}$EED$^{20}$ (FIG. 3F). Neither modification had any effect on basolateral targeting of Tac or of the GFP chimeric SCF constructs. However, the replacement of all three acidic residues 18, 19 and 20 with alanine residues (E-D18A-A) did alter basolateral sorting of the Tac-SCF chimeras. In clones expressing relatively low amounts of the Tac-E-D18A-A chimera, basolateral targeting was still efficient, however in clones expressing higher amounts of mutant Tac-SCF, both basolateral and apical surface staining was detected (FIG. 5D). Anti-Tac staining of these clones strongly resembled the phenotype already-seen with the d12-20 mutation (FIG. 4F). These data suggest, that the removal of the acidic cluster ($^{16}$EED$^{20}$) is the cause of the phenotype of the d12-20 mutation which results in a reduced efficiency of basolateral transport mediated by the monomeric leucine determinant.

iv) Comparison of the Basolateral Targeting Domain of SCF with that of CSF-1

SCF belongs to a large family of transmembrane growth factors that play important roles during development, tissue homeostasis and hematopoiesis. Based on sequence and functional homologies, SCF is most closely related to CSF-1. The similarities between the two factors extend to their respective receptor tyrosine kinases, c-fms, the receptor for CSF-1 and c-kit the receptor for SCF which are structurally conserved and which have evolved by chromosomal duplication. Sequence comparison (FIG. 6E) of the cytoplasmic domain of CSF-1 with that of SCF, reveals besides the most C-terminal valine residue, a leucine-containing motif at a position comparable to the basolateral targeting domain of SCF. However, the cluster of acidic amino acids N-terminal to this leucine motif is not conserved in CSF-1. In order to determine the basolateral sorting activities of CSF-1, the transmembrane and the cytoplasmic tail domains fused to the extracellular domain of Tac was expressed and its steady state distribution was studied in confluent monolayers of MDCK II cells (FIG. 6). The wildtype Tac-CSF-1 chimeric construct was expressed on the basolateral surface of MDCK II cells (FIG. 6C). However, a considerable amount of Tac-CSF-1 was also detected on the apical surface of confluent MDCK II cells (FIG. 6C'), a situation unlike the one observed with wildtype Tac-SCF chimeras (FIG. 6A, A'). The distribution of Tac-CSF-1 on basolateral as well as apical surfaces gave the impression that this construct is not sorted. In order to determine whether the homologous leucine in CSF-1 can interact with the sorting machinery of the cell, leucine 24 of CSF-1 was mutated to alanine. The respective Tac chimera (Tac-CSF-L24A) accumulated apically (FIG. 6D'), similar to Tac-SCF-L26 A (FIG. 6D'), suggesting that the leucine at the respective position in CSF-1 is nevertheless recognized as a basolateral sorting signal, but that the efficiency of basolateral transport is lower compared to that of wildtype SCF. This difference may depend on the presence of the acidic cluster in SCF which is absent from CSF-1.

v) In Contrast to Wildtype, the Mutant Cytoplasmic Tail of Mgf$^{Sl17H}$ SCF Induces Constitutive Endocytosis Closer inspection of cells transfected with C-terminal deletion mutants (d29, d36) showed increased accumulation of SCF-GFP and Tac-SCF within the cell body (shown for Tac-SCF, FIGS. 4C, D). This intracellular accumulation could be due to retention of newly synthesized SCF in the ER (see FIG. 9), or to endocytosis of cell surface SCF. Endocytosis was tested by the internalization of anti-Tac antibodies into Tac-SCF transfected cells.

Many basolateral sorting determinants have been shown to induce endocytosis, for example the basolateral targeting motif (ML) in the Invariant chain of the major histocompatibility complex II also mediates endocytosis of the respective proteins (11). Therefore, it was tested whether the wildtype cytoplasmic tail of SCF, expressed as a Tac chimera (Tac-SCF) was able to internalize Tac-SCF/anti-Tac complexes in non-polarized COS-7 cells. Anti-Tac antibodies were bound to transfected cells in the cold. Subsequently, Tac-SCF/anti-Tac antibody complexes were allowed to internalize at 37° C. and visualized after acid removal of cell surface remaining anti-Tac antibodies. Wildtype Tac-SCF expressing cells (FIG. 7B), as well as cells expressing various C-terminal deletions (d36, d29 and d22) or C-terminal valine substitutions (V36Q, add37Q) were analysed for internalization of anti-Tac antibodies. With the exception of the d29 mutation, all constructs showed similar low amounts of internalized antibodies. Interestingly, Tas-SCF carrying the d29 mutation was internalized to moderate levels, while the deletion encompassing the ML motif (d22) was not internalized, comparable to wildtype. This suggests that the removal of the C-terminal charged cluster changes the conformation of the basolateral targeting motif in such a way that moderate internalization of SCF via this ML (di-leucine like) motif can occur (see FIG. 2A). In other words, this suggests that the mono-leucine determinant in SCF does not induce endocytosis, a finding that is consistent with the persistent cell surface expression of membrane bound SCF. Many basolateral targeting signals resemble those for coated pit localization and endocytosis. In contrast to the protease furin or the Invariant chain, wildtype SCF is expressed at the cell surface and is not endocytosed. Interestingly, the cytoplasmic tail of SCF found in the Mgf$^{Sl17H}$ mutation has a high capacity to induce endocytosis when expressed as a Tac chimera. Analysis of the cytoplasmic tail of the Mgf$^{Sl17H}$ mutant reveal a match of sequence between KYAATERERISRGVIV$\underline{D}$VST$\underline{LL}$PSHSGW (SEQ ID NO: 56) (5), and the signal for endocytosis or lysosomal/melanosomal/vacuoler targeting (DxxxLL). This sequence was found in CD3 (DxxxLL) and in related form in the Invariant chain (DDQxxLI; ExxxML) (17), Vam3p (ExxxLL), LIMP II (EExxxLL) and tyrosinase (D/EExxxLL) (see 11 for a review). In all these proteins, the endocytotic activity is critically dependent on the presence of the di-leucine motif and is lost after alanine mutagenesis similar to the observations for the Mgf$^{Sl17H}$ mutation presented above.

Therefore the Mgf$^{Sl17H}$ mutation may represent a gain of function in respect to endocytosis and lysosomal targeting of SCF. As a consequence, only a limited amount of mutant SCF would be available on the cell surface to stimulate responsive, c-kit expressing neighboring cells. This could be the cause for the reduced amount of peripheral SCF dependent mast cells and a limited capacity to support hematopoiesis as observed in Mgf$^{Sl17H}$ mutant animals (6,7). In contrast, based on the data presented in this application, wildtype SCF lacks a signal for endocytosis and this is consistent with the role of the cytoplasmic tail of SCF for continuous presentation and signaling of the noncleavable form of SCF towards responsive cells.

Example 5

Gain of Function Mutations

In contrast to wildtype SCF, GFP and Tac-SCF chimeras containing the cytoplasmic tail of the Mgf$^{Sl17H}$ mutation accumulated in intracellular vesicular structures (Tac-SCF-17H, FIG. 7D; see also (8)). This intracellular accumulation of the mutant constructs, could be due to retention of newly synthesized chimeric proteins in the ER, or due to endocytosis of cell surface SCF. In order to determine, whether the intracellular steady state localization of Tac-SCF-17H in polarized MDCK II was the result of endocytosis (FIG. 7D), the localization was compared with that of a tyrosinase-Tac chimera (Tac-tyr). Tyrosinase is a protein that carries an established signal for endocytosis and lysosomal/melanosomal targeting and is therefore constitutively internalized from the cell surface (11). Interestingly, in polarized MDCK II cells, Tac-tyr localized to intracellular vesicular structures (FIG. 7G), resembling the staining seen for the Tac-SCF-17H construct (FIG. 7D). Sequence analysis of the cytoplasmic domain of Mgf$^{Sl17H}$ (KYAATERERISRGVIV$\underline{D}$VST$\underline{LL}$PSHSGW; (SEQ ID NO: 56) (5)) revealed a sequence homologous to the signal for endocytosis and lysosomal/melanosomal targeting, identified in tyrosinase, LIMP II and CD3 ($D^{17}$xxxLL$^{22}$) (see 11). Furthermore, mutation of the leucine residues ($L^{21}L^{22}$) which are part of this putative motif in Mgf$^{Sl17H}$ to alanines resulted in the loss of intracellular but led to apical accumulation of Tac-17H-LLAA in polarized MDCK cells (FIG. 7J). In addition, using the anti-Tac internalization assay in COS-7 cells, it was tested whether the intracellular localization of the Mgf$^{Sl17H}$ mutant was due to increased endocytosis of surface expressed Mgf$^{Sl17H}$ Tac chimeras. Indeed, compared to wildtype Tac-SCF, significantly more Tac-SCF-17H/anti-Tac complexes were internalized (FIG. 7E), and a similar intracellular staining pattern was observed as for the Tac-tyr construct (FIG. 7H). Furthermore, internalization of the Tac-SCF-17H chimera was blocked by the di-leucine mutation (17H-LLAA, FIG. 7K). This suggests, that the reduced amount of cell surface SCF observed in the Mgf$^{Sl17H}$ mutation (8) is due to constitutive removal of Mgf$^{Sl17H}$ mutant SCF from the cell surface by endocytosis. Therefore, the Mgf$^{Sl17H}$ mutation represents a molecular gain of function mutation in respect to endocytosis of SCF.

Example 6

The C-Terminal Valine is Required for Efficient ER to Golgi Transport and Efficient Exposure at the Cell Surface GFP tagged SCF constructs as described above were used in the experiment. To do a pulse chase experiment, the formation of the fluorophore of GFP is used as a timer. It has been demonstrated that the fluorophore of GFP is formed within 30 minutes after the synthesis of GFP at the ribosome (Chalfie and Kain, 1998). Therefore, within this time window, newly translated GFP fusion proteins are invisible to the observer in live cells. As a consequence, wildtype SCF-GFP fusion proteins can only be observed on the cell surface or post-Golgi transport vesicles (FIGS. 9A, G). When the C-terminal valine is removed (FIGS. 9B, H), replaced with glutamine or additional sequences are added to the valine (see FIG. 2A), the SCF-GFP chimeric protein can be seen to accumulate in the ER compartment. This localization has been verified by double staining for calreticulin a specific marker for the ER compartment (data not shown). Consequently, all mutant constructs lacking the c-terminal valine are retained in the ER and cell surface transport is delayed and occurs through the bulk protein flow from the ER to the cell surface. The reduced ER export results in reduced steady state levels of cell surface SCF. The amount of wildtype SCF-GFP construct was set to 100% expression levels, measured by surface biotinylation of transiently transfected COS-7 cells (fibroblasts), avidin precipitation and subsequent anti-SCF blotting (8). Cells were tested for the expression of identical amounts of protein independently (8). A removal of the C-terminal value residue resulted in the surface expression of 61% of wildtype constructs, while the 17H construct was only expressed to 21%. Various deletion mutants encompassing the cytoplasmic tail showed expression between 40–60% (e.g. d5 construct 41%). Surface expression of a construct lacking a transmembrane anchor was not detected. Therefore, a block of this valine determinant in vivo, would result in a reduced expression of SCF at the cell surface. Consequently, CSF-1, according to the invention, requires the same cytoplasmic conserved valine residue for export from the ER and efficient exposure at the cell surface.

Example 7

Alteration of Polarized as Well as Cell Surface Expression by Competitive Inhibition by the Cytoplasmic Tail (FIG. 10)

Figure 12:
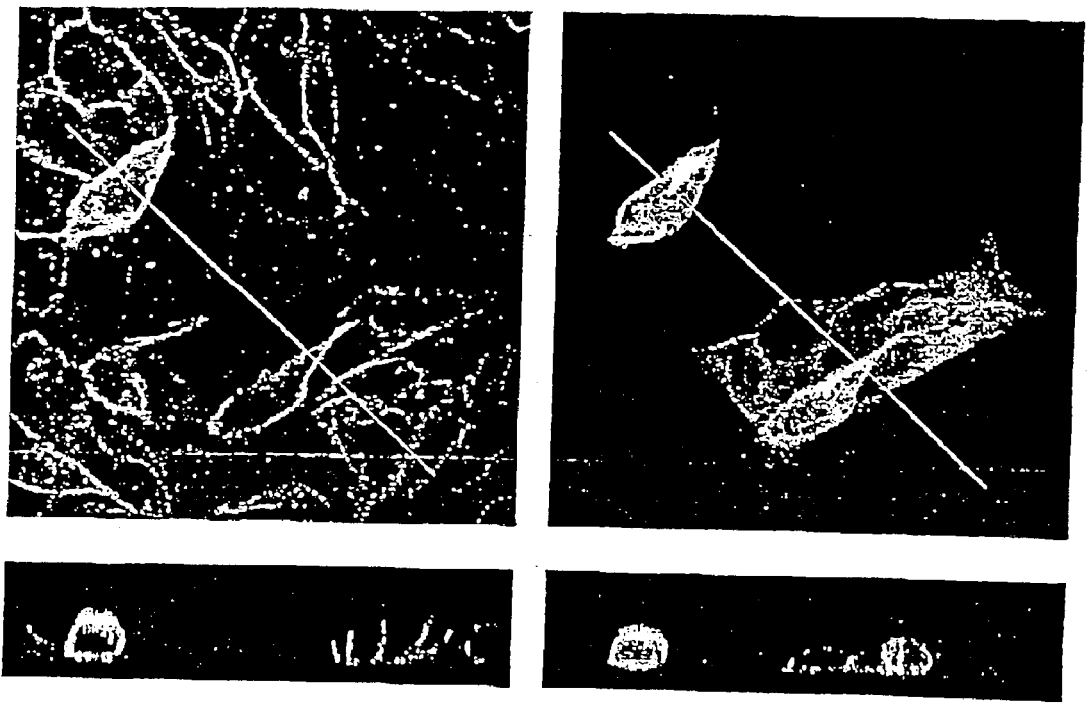

A CMV promoter driven fusion protein of GFP with the wildtype cytoplasmic tail of SCF (GFP-SCF-CT) was created. This construct is expressed in the cytoplasma, where it can accumulate to high expression levels due to overexpression. In FIGS. 11 and 12, examples are shown of confluent MDCK II cells expressing GFP-SCF-CT (FIGS. 11A and 12B) as well as wildtype transmembrane Tac-SCF as a reporter for basolateral expression (FIGS. 11B and 12A). FIG. 11 shows that in cells expressing moderate amounts of GFP-SCF-CT, the basolateral expression of the Tac-SCF reporter is not altered. However, in cells expressing the soluble cytoplasmic tail of SCF in high amounts (coupled to GFP) the normal localization of the transmembrane reporter construct at the lateral membranes is disrupted, which results in apical and intracellular accumulation. A similar situation is shown in FIG. 12, where a confocal section was performed (upper panel), below each panel, a corresponding Z-scan is shown below (the Z-scan has been performed along the indicated white line). Again, in highly expressing GFP-SCF-CT cells, the transmembrane Tac-SCF reporter construct accumulates apically in contrast to low expressers (group of cells to the right).

These results demonstrate that the development of an inhibitor based on competition with the determinant as well as inhibitors that cover the specific determinants in the cytoplasmic tail of SCF and CSF-1 (basolateral targeting domain as well as c-terminal valine) could be developed and would be functional in changing the localization of SCF and CSF-1 in vivo.

References

3. Flanagan, J. G., Chan, D. C., and Leder, P. (1991) *Cell* 64(5), 1025–35
4. Motro, B., Wojtowicz, J. M., Bernstein, A., and van der Kooy, D. (1996) *Proc Natl Acad Sci USA* 93(5), 1808–13
5. Brannan, C. I., Bedell, M. A., Resnick, J. L., Eppig, J. J., Handel, M. A., Williams, D. E., Lyman, S. D., Donovan, P. J., Jenkins, N. A., and Copeland, N. G. (1992) *Genes Dev* 6(10), 1832–42
6. Kapur, R., Cooper, R., Xiao, X., Weiss, M. J., Donovan, P., and Williams, D. A. (1999) *Blood* 94(6), 1915–25
7. Tajima, Y., Huang, E. J., Vosseller, K., Ono, M., Moore, M. A., and Besmer, P. (1998) *J Exp Med* 187(9), 1451–61
8. Wehrle-Haller, B., and Weston, J. A. (1999) *Dev Biol* 210(1), 71–86
11. Heilker, R., Spiess, M., and Crottet, P. (1999) *Bioessays* 21(7), 558–67
16. Matter, K., Yamamoto, E. M., and Mellman, I. (1994) *J Cell Biol* 126(4), 991–1004
17. Simonsen, A., Bremnes, B., Nordeng, T. W., and Bakke, O. (1998) *Eur J Cell Biol* 76(1), 25–32
19. Wan, L., Molloy, S. S., Thomas, L., Liu, G., Xiang, Y., Rybak, S. L., and Thomas, G. (1998) *Cell* 94(2), 205–16
20. Huang, E. J., Nocka, K. H., Buck, J., and Besmer, P. (1992) *Mol Biol Cell* 3(3), 349–62
25. Simmen, T., Nobile, M., Bonifacino, J. S., and Hunziker, W. (1999) *Mol Cell Biol* 19(4), 3136–44
30. Simmen, T., Schmidt, A., Hunziker, W., and Beermann, F. (1999) *J Cell Sci* 112(Pt 1), 45–53
35. Reich, V., Mostov, K.; and Aroeti, B. (1996) *J Cell Sci* 109(Pt 8), 2133–9

---

What is claim is:

1. A peptide or protein comprising a basolateral sorting signal consisting of the amino acid sequence:

$X_1h_2X_3h_4Leup_5p_6$ (SEQ ID NO: 1), wherein:
$X_1$ represents a glutamine acid (E), a glutamine (Q), or an alanine (A) residue,
$h_2$ represents an isolueucine (I) or an alanine (A) residue,
$X_3$ represents a serine (S), an alanine (A), or an aspartic acid (N) residue,
$h_4$ represents a methionine (M) or an alanine (A) residue,
$p_5$ represents a glutamine (Q) or asparagine (N) residue, and
$p_6$ represents a glutamine (Q) or a glutamic acid (E) residue, and wherein said peptide or protein comprises up to 50 amino acids.

2. The peptide or protein according to claim 1 further comprising at least one acidic cluster.

3. The peptide or protein according to claim 2 wherein said at least one acidic cluster comprises at least two acidic amino acids selected from the group consisting of glutamic acid (E) and aspartic acid (D).

4. The peptide or protein according to claim 2 wherein said at least one acidic cluster comprises the amino acid sequence EED, or QEE, EAE or EKD.

5. The peptide or protein according to claim 2, wherein said at least one acidic cluster is N-terminal to the basolateral sorting signal.

6. The peptide or protein according to claim 1 further comprising a cluster of at least 4 consecutive charged amino acids.

7. The peptide or protein according to claim 6, wherein said 4 consecutive charged amino acids are alternatively positively and negatively charged.

8. The peptide or protein according to claim 6, wherein said 4 consecutive charged amino acids are KERE SEQ ID NO: 19), KEKE (SEQ ID NO: 20), DEDR (SEQ ID NO: 75), or EEDR (SEQ ID NO: 21), where K represents a lysine residue, E a glutamic acid residue, R an arginine residue and D an aspartic acid residue.

9. The peptide or protein according to claim 6, wherein said 4 consecutive charged amino acids are C-terminal to the basolateral sorting signal.

10. The peptide or protein according to claim 1 further comprising a valine at its C-terminus.

11. The peptide or protein according to claim 1, wherein $X_1$ represents a glutamic acid (E), $h_2$ represents an isoleucine (I) residue, $X_3$ represents a serine (S) residue, $h_4$ represents a methionine (M) residue, $p_5$ represents a glutamine (Q) residue, and $p_6$ represents a glutamic acid (E) residue.

* * * * *

UNITED STATES PATENT AND TRADEMARK OFFICE
CERTIFICATE OF CORRECTION

PATENT NO.          : 7,033,794 B2
APPLICATION NO. : 10/176791
DATED                  : April 25, 2006
INVENTOR(S)        : Wehrle-Haller et al.

It is certified that error appears in the above-identified patent and that said Letters Patent is hereby corrected as shown below:

Column 2, Line 3, replace "also be found" with --also found--.

Column 4, Line 29, replace "golgi network" with --Golgi network--.

Column 5, Line 23, replace "Acidic amino acid" with --Acidic amino acids--.

Column 6, Line 17, replace "$X_1h_2X_3h_4L+eep_5p_6$" with --$X_1h_2X_3h_4\underline{L}p_5p_6$--.

Column 7, Line 13, replace "upto" with --up to--.

Column 11, Line 37, replace "molecules" with --molecule--.

Column 12, Line 64, replace "basoateral" with --basolateral--.

Column 16, Line 10, replace "seguence" with --sequence--.

Column 17, Line 3, replace "wildtpye" with --wildtype--.

Column 18, Line 4, replace "oogonesis" with --oogenesis--.

Column 20, Line 11, replace "determinant" with --determinant.--.

Column 21, Line 46, replace "exppression" with --expression--.

Column 63, Line 18, replace "KERE SEQ ID" with --KERE (SEQ ID--.

Signed and Sealed this

Tenth Day of October, 2006

JON W. DUDAS
*Director of the United States Patent and Trademark Office*

SEQUENCE LISTING

<160> NUMBER OF SEQ ID NOS: 78

<210> SEQ ID NO 1
<211> LENGTH: 7
<212> TYPE: PRT
<213> ORGANISM: Artificial Sequence
<220> FEATURE:
<223> OTHER INFORMATION: Mono-Leucine Basolateral Sorting Signal
<220> FEATURE:
<221> NAME/KEY: VARIANT
<222> LOCATION: 1
<223> OTHER INFORMATION: Xaa = Glu, Ala, Ser, Thr, Asn, Gln, Tyr, Lys, Arg, or Asp.
<220> FEATURE:
<221> NAME/KEY: VARIANT
<222> LOCATION: 2
<223> OTHER INFORMATION: Xaa= Ile, Gly, Ala, Pro, Cys, Val, Leu, Phe, Met, or Trp.
<220> FEATURE:
<221> NAME/KEY: VARIANT
<222> LOCATION: 3
<223> OTHER INFORMATION: Xaa=any amino acid.
<220> FEATURE:
<221> NAME/KEY: VARIANT
<222> LOCATION: 4
<223> OTHER INFORMATION: Xaa= Met, Gly, Ala, Pro, Cys, Val, Phe, or Trp.

```
<220> FEATURE:
<221> NAME/KEY: VARIANT
<222> LOCATION: 6
<223> OTHER INFORMATION: Xaa= Gln, Ser, Thr, Asn, Tyr, Lys, Arg, Asp, or
      Glu.
<220> FEATURE:
<221> NAME/KEY: VARIANT
<222> LOCATION: (7)...(7)
<223> OTHER INFORMATION: Xaa=Glu, Ser, Thr, Asn, Gln, Tyr, Lys, Arg, or
      Asp.

<400> SEQUENCE: 1

Xaa Xaa Xaa Xaa Leu Xaa Xaa
 1               5

<210> SEQ ID NO 2
<211> LENGTH: 7
<212> TYPE: PRT
<213> ORGANISM: Artificial Sequence
<220> FEATURE:
<223> OTHER INFORMATION: Mono-Leucine Basolateral Sorting Signal

<400> SEQUENCE: 2

Glu Ile Ser Met Leu Gln Gln
 1               5

<210> SEQ ID NO 3
<211> LENGTH: 7
<212> TYPE: PRT
<213> ORGANISM: Artificial Sequence
<220> FEATURE:
<223> OTHER INFORMATION: Mono-Leucine Basolateral Sorting Signal

<400> SEQUENCE: 3

Glu Ile Ser Met Leu Gln Glu
 1               5

<210> SEQ ID NO 4
<211> LENGTH: 7
<212> TYPE: PRT
<213> ORGANISM: Artificial Sequence
<220> FEATURE:
<223> OTHER INFORMATION: Mono-Leucine Basolateral Sorting Signal

<400> SEQUENCE: 4

Ala Ile Ser Met Leu Gln Gln
 1               5

<210> SEQ ID NO 5
<211> LENGTH: 7
<212> TYPE: PRT
<213> ORGANISM: Artificial Sequence
<220> FEATURE:
<223> OTHER INFORMATION: Mono-Leucine Basolateral Sorting Signal

<400> SEQUENCE: 5

Ala Ile Ser Met Leu Gln Glu
 1               5

<210> SEQ ID NO 6
<211> LENGTH: 7
<212> TYPE: PRT
<213> ORGANISM: Artificial Sequence
<220> FEATURE:
<223> OTHER INFORMATION: Mono-Leucine Basolateral Sorting Signal

<400> SEQUENCE: 6

Gln Ile Ser Met Leu Gln Gln
```

```
<210> SEQ ID NO 7
<211> LENGTH: 7
<212> TYPE: PRT
<213> ORGANISM: Artificial Sequence
<220> FEATURE:
<223> OTHER INFORMATION: Mono-Leucine Basolateral Sorting Signal

<400> SEQUENCE: 7

Gln Ile Ser Met Leu Gln Glu
 1               5

<210> SEQ ID NO 8
<211> LENGTH: 7
<212> TYPE: PRT
<213> ORGANISM: Artificial Sequence
<220> FEATURE:
<223> OTHER INFORMATION: Mono-Leucine Basolateral Sorting Signal

<400> SEQUENCE: 8

Glu Ala Ser Met Leu Gln Gln
 1               5

<210> SEQ ID NO 9
<211> LENGTH: 7
<212> TYPE: PRT
<213> ORGANISM: Artificial Sequence
<220> FEATURE:
<223> OTHER INFORMATION: Mono-Leucine Basolateral Sorting Signal

<400> SEQUENCE: 9

Glu Ala Ser Met Leu Gln Glu
 1               5

<210> SEQ ID NO 10
<211> LENGTH: 7
<212> TYPE: PRT
<213> ORGANISM: Artificial Sequence
<220> FEATURE:
<223> OTHER INFORMATION: Mono-Leucine Basolateral Sorting Signal

<400> SEQUENCE: 10

Glu Ile Asp Met Leu Gln Gln
 1               5

<210> SEQ ID NO 11
<211> LENGTH: 7
<212> TYPE: PRT
<213> ORGANISM: Artificial Sequence
<220> FEATURE:
<223> OTHER INFORMATION: Mono-Leucine Basolateral Sorting Signal

<400> SEQUENCE: 11

Glu Ile Asp Met Leu Gln Glu
 1               5

<210> SEQ ID NO 12
<211> LENGTH: 7
<212> TYPE: PRT
<213> ORGANISM: Artificial Sequence
<220> FEATURE:
<223> OTHER INFORMATION: Mono-Leucine Basolateral Sorting Signal

<400> SEQUENCE: 12

Glu Ile Ala Met Leu Gln Gln
 1               5
```

```
<210> SEQ ID NO 13
<211> LENGTH: 7
<212> TYPE: PRT
<213> ORGANISM: Artificial Sequence
<220> FEATURE:
<223> OTHER INFORMATION: Mono-Leucine Basolateral Sorting Signal

<400> SEQUENCE: 13

Glu Ile Ala Met Leu Gln Glu
1               5

<210> SEQ ID NO 14
<211> LENGTH: 7
<212> TYPE: PRT
<213> ORGANISM: Artificial Sequence
<220> FEATURE:
<223> OTHER INFORMATION: Mono-Leucine Basolateral Sorting Signal

<400> SEQUENCE: 14

Glu Ile Ser Ala Leu Gln Gln
1               5

<210> SEQ ID NO 15
<211> LENGTH: 7
<212> TYPE: PRT
<213> ORGANISM: Artificial Sequence
<220> FEATURE:
<223> OTHER INFORMATION: Mono-Leucine Basolateral Sorting Signal

<400> SEQUENCE: 15

Glu Ile Ser Ala Leu Gln Glu
1               5

<210> SEQ ID NO 16
<211> LENGTH: 7
<212> TYPE: PRT
<213> ORGANISM: Artificial Sequence
<220> FEATURE:
<223> OTHER INFORMATION: Mono-Leucine Basolateral Sorting Signal

<400> SEQUENCE: 16

Glu Ile Ser Met Leu Asn Gln
1               5

<210> SEQ ID NO 17
<211> LENGTH: 7
<212> TYPE: PRT
<213> ORGANISM: Artificial Sequence
<220> FEATURE:
<223> OTHER INFORMATION: Mono-Leucine Basolateral Sorting Signal

<400> SEQUENCE: 17

Glu Ile Ser Met Leu Asn Glu
1               5

<210> SEQ ID NO 18
<211> LENGTH: 7
<212> TYPE: PRT
<213> ORGANISM: Artificial Sequence
<220> FEATURE:
<223> OTHER INFORMATION: Mono-Leucine Basolateral Sorting Signal

<400> SEQUENCE: 18

Gln Ala Ser Met Leu Asn Gln
1               5
```

```
<210> SEQ ID NO 19
<211> LENGTH: 4
<212> TYPE: PRT
<213> ORGANISM: Artificial Sequence
<220> FEATURE:
<223> OTHER INFORMATION: Cluster of Charged Amino-Acids

<400> SEQUENCE: 19

Lys Glu Arg Glu
 1

<210> SEQ ID NO 20
<211> LENGTH: 4
<212> TYPE: PRT
<213> ORGANISM: Artificial Sequence
<220> FEATURE:
<223> OTHER INFORMATION: Cluster of Charged Amino-Acids

<400> SEQUENCE: 20

Lys Glu Lys Glu
 1

<210> SEQ ID NO 21
<211> LENGTH: 4
<212> TYPE: PRT
<213> ORGANISM: Artificial Sequence
<220> FEATURE:
<223> OTHER INFORMATION: Cluster of Charged Amino-Acids

<400> SEQUENCE: 21

Glu Glu Asp Arg
 1

<210> SEQ ID NO 22
<211> LENGTH: 21
<212> TYPE: PRT
<213> ORGANISM: Artificial Sequence
<220> FEATURE:
<223> OTHER INFORMATION: Junction of SCF-EGFP Chimera with MYC Tag

<400> SEQUENCE: 22

Ser Ser Thr Leu Gly Pro Glu Gln Lys Leu Ile Ser Glu Glu Asp Leu
 1               5                  10                  15
Gly Gln Ser Ile Val
            20

<210> SEQ ID NO 23
<211> LENGTH: 11
<212> TYPE: PRT
<213> ORGANISM: Artificial Sequence
<220> FEATURE:
<223> OTHER INFORMATION: Junction of EGFP-SCF Chimera

<400> SEQUENCE: 23

Tyr Lys Thr Gly Pro Glu Lys Asp Ser Arg Val
 1               5                  10

<210> SEQ ID NO 24
<211> LENGTH: 15
<212> TYPE: PRT
<213> ORGANISM: Artificial Sequence
<220> FEATURE:
<223> OTHER INFORMATION: Junction Between Extracellular Domain and
      Transmembrane Domain of Tac-SCF Chimera

<400> SEQUENCE: 24
```

-continued

Ser Ile Phe Thr Thr Asp Leu Gln Trp Thr Ala Met Ala Leu Pro
1               5                   10                  15

<210> SEQ ID NO 25
<211> LENGTH: 26
<212> TYPE: DNA
<213> ORGANISM: Artificial Sequence
<220> FEATURE:
<223> OTHER INFORMATION: Primer

<400> SEQUENCE: 25
aacagatctc cagatccctg agtctg                                        26

<210> SEQ ID NO 26
<211> LENGTH: 28
<212> TYPE: DNA
<213> ORGANISM: Artificial Sequence
<220> FEATURE:
<223> OTHER INFORMATION: Primer

<400> SEQUENCE: 26
aacagatctc caagccagtc gtatctgg                                      28

<210> SEQ ID NO 27
<211> LENGTH: 17
<212> TYPE: PRT
<213> ORGANISM: Artificial Sequence
<220> FEATURE:
<223> OTHER INFORMATION: Junction of Tac-CSF-1 Chimera

<400> SEQUENCE: 27

Ser Ile Phe Thr Asp Leu Gln Ile Pro Glu Ser Val Phe His Leu Leu
1               5                   10                  15

Val

<210> SEQ ID NO 28
<211> LENGTH: 8
<212> TYPE: PRT
<213> ORGANISM: Artificial Sequence
<220> FEATURE:
<223> OTHER INFORMATION: Junction of Tac-EGFP Chimera

<400> SEQUENCE: 28

Thr Ile Gln Ala Ser Thr Met Val
1               5

<210> SEQ ID NO 29
<211> LENGTH: 8
<212> TYPE: PRT
<213> ORGANISM: Artificial Sequence
<220> FEATURE:
<223> OTHER INFORMATION: Sequence Comprising Basolateral Sorting Signal

<400> SEQUENCE: 29

Asn Glu Ile Ser Met Leu Gln Gln
1               5

<210> SEQ ID NO 30
<211> LENGTH: 9
<212> TYPE: PRT
<213> ORGANISM: Artificial Sequence
<220> FEATURE:
<223> OTHER INFORMATION: Sequence N-Terminal to Basolateral Sorting
      Signal

<400> SEQUENCE: 30

Glu Asn Ile Gln Ile Asn Glu Glu Asp
1               5

<210> SEQ ID NO 31
<211> LENGTH: 6
<212> TYPE: PRT
<213> ORGANISM: Artificial Sequence
<220> FEATURE:
<223> OTHER INFORMATION: Sequence Comprising Basolateral Sorting Signal
<220> FEATURE:
<221> NAME/KEY: VARIANT
<222> LOCATION: 2, 3, 4
<223> OTHER INFORMATION: Xaa = Any Amino Acid

<400> SEQUENCE: 31

Glu Xaa Xaa Xaa Met Leu
1               5

<210> SEQ ID NO 32
<211> LENGTH: 6
<212> TYPE: PRT
<213> ORGANISM: Artificial Sequence
<220> FEATURE:
<223> OTHER INFORMATION: Sequence Comprising Basolateral Sorting Signal
<220> FEATURE:
<221> NAME/KEY: VARIANT
<222> LOCATION: 2, 3, 4
<223> OTHER INFORMATION: Xaa = Any Amino Acid

<400> SEQUENCE: 32

Ala Xaa Xaa Xaa Met Leu
1               5

<210> SEQ ID NO 33
<211> LENGTH: 36
<212> TYPE: PRT
<213> ORGANISM: Mus musculus

<400> SEQUENCE: 33

Lys Lys Lys Gln Ser Ser Leu Thr Arg Ala Val Glu Asn Ile Gln Ile
1               5                   10                  15

Asn Glu Glu Asp Asn Glu Ile Ser Met Leu Gln Gln Lys Glu Arg Glu
            20                  25                  30

Phe Gln Glu Val
        35

<210> SEQ ID NO 34
<211> LENGTH: 35
<212> TYPE: PRT
<213> ORGANISM: Artificial Sequence
<220> FEATURE:
<223> OTHER INFORMATION: Cytoplasmic Tail of d36 Mutant

<400> SEQUENCE: 34

Lys Lys Lys Gln Ser Ser Leu Thr Arg Ala Val Glu Asn Ile Gln Ile
1               5                   10                  15

Asn Glu Glu Asp Asn Glu Ile Ser Met Leu Gln Gln Lys Glu Arg Glu
            20                  25                  30

Phe Gln Glu
        35

<210> SEQ ID NO 35
<211> LENGTH: 28
<212> TYPE: PRT
<213> ORGANISM: Artificial Sequence
<220> FEATURE:

```
<223> OTHER INFORMATION: Cytoplasmic Tail of d29 Mutant

<400> SEQUENCE: 35

Lys Lys Lys Gln Ser Ser Leu Thr Arg Ala Val Glu Asn Ile Gln Ile
 1               5                  10                  15

Asn Glu Glu Asp Asn Glu Ile Ser Met Leu Gln Gln
            20                  25

<210> SEQ ID NO 36
<211> LENGTH: 21
<212> TYPE: PRT
<213> ORGANISM: Artificial Sequence
<220> FEATURE:
<223> OTHER INFORMATION: Cytoplasmic Tail of d22 Mutant

<400> SEQUENCE: 36

Lys Lys Lys Gln Ser Ser Leu Thr Arg Ala Val Glu Asn Ile Gln Ile
 1               5                  10                  15

Asn Glu Glu Asp Asn
            20

<210> SEQ ID NO 37
<211> LENGTH: 11
<212> TYPE: PRT
<213> ORGANISM: Artificial Sequence
<220> FEATURE:
<223> OTHER INFORMATION: Cytoplasmic Tail of d12 Mutant

<400> SEQUENCE: 37

Lys Lys Lys Gln Ser Ser Leu Thr Arg Ala Val
 1               5                  10

<210> SEQ ID NO 38
<211> LENGTH: 28
<212> TYPE: PRT
<213> ORGANISM: Artificial Sequence
<220> FEATURE:
<223> OTHER INFORMATION: Cytoplasmic Tail of d21-28 Mutant

<400> SEQUENCE: 38

Lys Lys Lys Gln Ser Ser Leu Thr Arg Ala Val Glu Asn Ile Gln Ile
 1               5                  10                  15

Asn Glu Glu Asp Lys Glu Arg Glu Phe Gln Glu Val
            20                  25

<210> SEQ ID NO 39
<211> LENGTH: 19
<212> TYPE: PRT
<213> ORGANISM: Artificial Sequence
<220> FEATURE:
<223> OTHER INFORMATION: Cytoplasmic Tail of d12-28 Mutant

<400> SEQUENCE: 39

Lys Lys Lys Gln Ser Ser Leu Thr Arg Ala Val Lys Glu Arg Glu Phe
 1               5                  10                  15

Gln Glu Val

<210> SEQ ID NO 40
<211> LENGTH: 20
<212> TYPE: PRT
<213> ORGANISM: Artificial Sequence
<220> FEATURE:
<223> OTHER INFORMATION: Cytoplasmic Tail of d5-20 Mutant

<400> SEQUENCE: 40
```

```
Lys Lys Lys Gln Asn Glu Ile Ser Met Leu Gln Gln Lys Glu Arg Glu
 1               5                  10                  15

Phe Gln Glu Val
            20
```

<210> SEQ ID NO 41
<211> LENGTH: 27
<212> TYPE: PRT
<213> ORGANISM: Artificial Sequence
<220> FEATURE:
<223> OTHER INFORMATION: Cytoplasmic Tail of d12-20 Mutant

<400> SEQUENCE: 41

```
Lys Lys Lys Gln Ser Ser Leu Thr Arg Ala Val Asn Glu Ile Ser Met
 1               5                  10                  15

Leu Gln Gln Lys Glu Arg Glu Phe Gln Glu Val
            20                  25
```

<210> SEQ ID NO 42
<211> LENGTH: 36
<212> TYPE: PRT
<213> ORGANISM: Artificial Sequence
<220> FEATURE:
<223> OTHER INFORMATION: Cytoplasmic Tail of S24A Mutant

<400> SEQUENCE: 42

```
Lys Lys Lys Gln Ser Ser Leu Thr Arg Ala Val Glu Asn Ile Gln Ile
 1               5                  10                  15

Asn Glu Glu Asp Asn Glu Ile Ala Met Leu Gln Gln Lys Glu Arg Glu
            20                  25                  30

Phe Gln Glu Val
            35
```

<210> SEQ ID NO 43
<211> LENGTH: 36
<212> TYPE: PRT
<213> ORGANISM: Artificial Sequence
<220> FEATURE:
<223> OTHER INFORMATION: Cytoplasmic Tail of S24D Mutant

<400> SEQUENCE: 43

```
Lys Lys Lys Gln Ser Ser Leu Thr Arg Ala Val Glu Asn Ile Gln Ile
 1               5                  10                  15

Asn Glu Glu Asp Asn Glu Ile Asp Met Leu Gln Gln Lys Glu Arg Glu
            20                  25                  30

Phe Gln Glu Val
            35
```

<210> SEQ ID NO 44
<211> LENGTH: 36
<212> TYPE: PRT
<213> ORGANISM: Artificial Sequence
<220> FEATURE:
<223> OTHER INFORMATION: Cytoplasmic Tail of L26A Mutant

<400> SEQUENCE: 44

```
Lys Lys Lys Gln Ser Ser Leu Thr Arg Ala Val Glu Asn Ile Gln Ile
 1               5                  10                  15

Asn Glu Glu Asp Asn Glu Ile Ser Met Ala Gln Gln Lys Glu Arg Glu
            20                  25                  30

Phe Gln Glu Val
            35
```

```
<210> SEQ ID NO 45
<211> LENGTH: 36
<212> TYPE: PRT
<213> ORGANISM: Artificial Sequence
<220> FEATURE:
<223> OTHER INFORMATION: Cytoplasmic Tail of M25A/L26A Mutant

<400> SEQUENCE: 45

Lys Lys Lys Gln Ser Ser Leu Thr Arg Ala Val Glu Asn Ile Gln Ile
 1               5                  10                  15

Asn Glu Glu Asp Asn Glu Ile Ser Ala Ala Gln Gln Lys Glu Arg Glu
             20                  25                  30

Phe Gln Glu Val
        35

<210> SEQ ID NO 46
<211> LENGTH: 36
<212> TYPE: PRT
<213> ORGANISM: Artificial Sequence
<220> FEATURE:
<223> OTHER INFORMATION: Cytoplasmic Tail of M25A Mutant

<400> SEQUENCE: 46

Lys Lys Lys Gln Ser Ser Leu Thr Arg Ala Val Glu Asn Ile Gln Ile
 1               5                  10                  15

Asn Glu Glu Asp Asn Glu Ile Ser Ala Leu Gln Gln Lys Glu Arg Glu
             20                  25                  30

Phe Gln Glu Val
        35

<210> SEQ ID NO 47
<211> LENGTH: 36
<212> TYPE: PRT
<213> ORGANISM: Artificial Sequence
<220> FEATURE:
<223> OTHER INFORMATION: Cytoplasmic Tail of E19K Mutant

<400> SEQUENCE: 47

Lys Lys Lys Gln Ser Ser Leu Thr Arg Ala Val Glu Asn Ile Gln Ile
 1               5                  10                  15

Asn Glu Lys Asp Asn Glu Ile Ser Met Leu Gln Gln Lys Glu Arg Glu
             20                  25                  30

Phe Gln Glu Val
        35

<210> SEQ ID NO 48
<211> LENGTH: 36
<212> TYPE: PRT
<213> ORGANISM: Artificial Sequence
<220> FEATURE:
<223> OTHER INFORMATION: Cytoplasmic Tail of E22A Mutant

<400> SEQUENCE: 48

Lys Lys Lys Gln Ser Ser Leu Thr Arg Ala Val Glu Asn Ile Gln Ile
 1               5                  10                  15

Asn Glu Glu Asp Asn Ala Ile Ser Met Leu Gln Gln Lys Glu Arg Glu
             20                  25                  30

Phe Gln Glu Val
        35

<210> SEQ ID NO 49
```

```
<211> LENGTH: 36
<212> TYPE: PRT
<213> ORGANISM: Artificial Sequence
<220> FEATURE:
<223> OTHER INFORMATION: Cytoplasmic Tail of E-D18A-A Mutant

<400> SEQUENCE: 49

Lys Lys Lys Gln Ser Ser Leu Thr Arg Ala Val Glu Asn Ile Gln Ile
  1               5                  10                  15

Asn Ala Ala Ala Asn Glu Ile Ser Met Leu Gln Gln Lys Glu Arg Glu
             20                  25                  30

Phe Gln Glu Val
         35

<210> SEQ ID NO 50
<211> LENGTH: 36
<212> TYPE: PRT
<213> ORGANISM: Artificial Sequence
<220> FEATURE:
<223> OTHER INFORMATION: Cytoplasmic Tail of S24A/L26S Mutant

<400> SEQUENCE: 50

Lys Lys Lys Gln Ser Ser Leu Thr Arg Ala Val Glu Asn Ile Gln Ile
  1               5                  10                  15

Asn Glu Glu Asp Asn Glu Ile Ala Met Ser Gln Gln Lys Glu Arg Glu
             20                  25                  30

Phe Gln Glu Val
         35

<210> SEQ ID NO 51
<211> LENGTH: 36
<212> TYPE: PRT
<213> ORGANISM: Artificial Sequence
<220> FEATURE:
<223> OTHER INFORMATION: Cytoplasmic Tail of M25L Mutant

<400> SEQUENCE: 51

Lys Lys Lys Gln Ser Ser Leu Thr Arg Ala Val Glu Asn Ile Gln Ile
  1               5                  10                  15

Asn Glu Glu Asp Asn Glu Ile Ser Leu Leu Gln Gln Lys Glu Arg Glu
             20                  25                  30

Phe Gln Glu Val
         35

<210> SEQ ID NO 52
<211> LENGTH: 36
<212> TYPE: PRT
<213> ORGANISM: Artificial Sequence
<220> FEATURE:
<223> OTHER INFORMATION: Cytoplasmic Tail of V26Q Mutant

<400> SEQUENCE: 52

Lys Lys Lys Gln Ser Ser Leu Thr Arg Ala Val Glu Asn Ile Gln Ile
  1               5                  10                  15

Asn Glu Glu Asp Asn Glu Ile Ser Met Leu Gln Gln Lys Glu Arg Glu
             20                  25                  30

Phe Gln Glu Gln
         35

<210> SEQ ID NO 53
<211> LENGTH: 37
<212> TYPE: PRT
<213> ORGANISM: Artificial Sequence
```

-continued

```
<220> FEATURE:
<223> OTHER INFORMATION: Cytoplasmic Tail of add37Q Mutant

<400> SEQUENCE: 53
```

Lys Lys Lys Gln Ser Ser Leu Thr Arg Ala Val Glu Asn Ile Gln Ile
1               5                   10                  15

Asn Glu Glu Asp Asn Glu Ile Ser Met Leu Gln Gln Lys Glu Arg Glu
            20                  25                  30

Phe Gln Glu Val Gln
        35

```
<210> SEQ ID NO 54
<211> LENGTH: 35
<212> TYPE: PRT
<213> ORGANISM: Artificial Sequence
<220> FEATURE:
<223> OTHER INFORMATION: Cytoplasmic Tail of L26A/d36 Mutant

<400> SEQUENCE: 54
```

Lys Lys Lys Gln Ser Ser Leu Thr Arg Ala Val Glu Asn Ile Gln Ile
1               5                   10                  15

Asn Glu Glu Asp Asn Glu Ile Ser Met Ala Gln Gln Lys Glu Arg Glu
            20                  25                  30

Phe Gln Glu
        35

```
<210> SEQ ID NO 55
<211> LENGTH: 28
<212> TYPE: PRT
<213> ORGANISM: Mus musculus

<400> SEQUENCE: 55
```

Lys Tyr Ala Ala Thr Glu Arg Glu Arg Ile Ser Arg Gly Val Ile Val
1               5                   10                  15

Asp Val Ser Thr Leu Leu Pro Ser His Ser Gly Trp
            20                  25

```
<210> SEQ ID NO 56
<211> LENGTH: 28
<212> TYPE: PRT
<213> ORGANISM: Artificial Sequence
<220> FEATURE:
<223> OTHER INFORMATION: Cytoplasmic Tail of SCF-17H (L20A/L21A) mutant

<400> SEQUENCE: 56
```

Lys Tyr Ala Ala Thr Glu Arg Glu Arg Ile Ser Arg Gly Val Ile Val
1               5                   10                  15

Asp Val Ser Thr Ala Ala Pro Ser His Ser Gly Trp
            20                  25

```
<210> SEQ ID NO 57
<211> LENGTH: 15
<212> TYPE: PRT
<213> ORGANISM: Mus musculus

<400> SEQUENCE: 57
```

Gln Arg Arg Gln Arg Lys Ser Arg Arg Thr Ile Gln Ala Ser Ser
1               5                   10                  15

```
<210> SEQ ID NO 58
<211> LENGTH: 36
<212> TYPE: PRT
<213> ORGANISM: Mus musculus
```

```
<400> SEQUENCE: 58

Arg Leu Cys Leu Gln Lys Lys Lys Lys Lys Gln Pro Gln Glu Glu
1               5                   10                  15

Arg Gln Pro Leu Leu Met Asp Lys Asp Asp Tyr His Ser Leu Leu Tyr
            20                  25                  30

Gln Ser His Leu
        35

<210> SEQ ID NO 59
<211> LENGTH: 36
<212> TYPE: PRT
<213> ORGANISM: Mus musculus

<400> SEQUENCE: 59

Lys Trp Lys Trp Arg Ser Arg Asp Pro Gln Thr Leu Asp Ser Ser Val
1               5                   10                  15

Gly Arg Pro Glu Asp Ser Ser Leu Thr Gln Asp Glu Asp Arg Gln Val
            20                  25                  30

Glu Leu Pro Val
        35

<210> SEQ ID NO 60
<211> LENGTH: 36
<212> TYPE: PRT
<213> ORGANISM: Artificial Sequence
<220> FEATURE:
<223> OTHER INFORMATION: Cytoplasmic Tail of CSF-1L24A Mutant

<400> SEQUENCE: 60

Lys Trp Lys Trp Arg Ser Arg Asp Pro Gln Thr Leu Asp Ser Ser Val
1               5                   10                  15

Gly Arg Pro Glu Asp Ser Ser Ala Thr Gln Asp Glu Asp Arg Gln Val
            20                  25                  30

Glu Leu Pro Val
        35

<210> SEQ ID NO 61
<211> LENGTH: 56
<212> TYPE: PRT
<213> ORGANISM: Homo sapiens

<400> SEQUENCE: 61

Met Ala Leu Pro Ala Leu Phe Ser Leu Ile Ile Gly Phe Ala Phe Gly
1               5                   10                  15

Ala Leu Tyr Trp Lys Lys Arg Gln Pro Ser Leu Thr Arg Ala Val Glu
            20                  25                  30

Asn Ile Gln Ile Asn Glu Glu Asp Asn Glu Ile Ser Met Leu Gln Glu
        35                  40                  45

Lys Glu Arg Glu Phe Gln Glu Val
    50                  55

<210> SEQ ID NO 62
<211> LENGTH: 56
<212> TYPE: PRT
<213> ORGANISM: Mus musculus

<400> SEQUENCE: 62

Met Ala Leu Pro Ala Leu Ile Ser Leu Val Ile Gly Phe Ala Phe Gly
1               5                   10                  15
```

```
Ala Leu Tyr Trp Lys Lys Gln Ser Ser Leu Thr Arg Ala Val Glu
            20                  25                  30

Asn Ile Gln Ile Asn Glu Glu Asp Asn Glu Ile Ser Met Leu Gln Gln
        35                  40                  45

Lys Glu Arg Glu Phe Gln Glu Val
    50                  55

<210> SEQ ID NO 63
<211> LENGTH: 56
<212> TYPE: PRT
<213> ORGANISM: Canis familiaris

<400> SEQUENCE: 63

Met Ala Leu Pro Ala Phe Phe Ser Leu Val Ile Gly Phe Ala Phe Gly
1               5                   10                  15

Ala Leu Tyr Trp Lys Lys Lys Gln Pro Asn Leu Thr Arg Thr Val Glu
            20                  25                  30

Asn Ile Gln Ile Asn Glu Glu Asp Asn Glu Ile Ser Met Leu Gln Glu
        35                  40                  45

Lys Glu Arg Glu Phe Gln Glu Val
    50                  55

<210> SEQ ID NO 64
<211> LENGTH: 49
<212> TYPE: PRT
<213> ORGANISM: Equus caballus

<400> SEQUENCE: 64

Met Ala Leu Pro Ala Phe Phe Ser Leu Val Ile Gly Phe Ala Phe Gly
1               5                   10                  15

Ala Leu Tyr Trp Lys Lys Lys Gln Pro Asn Leu Thr Arg Ala Val Glu
            20                  25                  30

Asn Ile Gln Ile Asn Glu Glu Asp Asn Glu Ile Ser Met Leu Gln Glu
        35                  40                  45

Lys

<210> SEQ ID NO 65
<211> LENGTH: 56
<212> TYPE: PRT
<213> ORGANISM: Bos Taurus

<400> SEQUENCE: 65

Val Ala Leu Pro Ala Phe Phe Ser Leu Val Ile Gly Phe Ala Phe Gly
1               5                   10                  15

Ala Phe Tyr Trp Lys Lys Lys Gln Pro Asn Leu Thr Arg Thr Val Glu
            20                  25                  30

Asn Arg Gln Ile Asn Glu Glu Asp Asn Glu Ile Ser Met Leu Gln Glu
        35                  40                  45

Lys Glu Arg Glu Phe Gln Glu Val
    50                  55

<210> SEQ ID NO 66
<211> LENGTH: 49
<212> TYPE: PRT
<213> ORGANISM: Ovis aries

<400> SEQUENCE: 66

Val Ala Leu Pro Ala Phe Phe Ser Leu Val Ile Gly Phe Ala Phe Gly
1               5                   10                  15
```

```
Ala Leu Tyr Trp Lys Lys Lys Gln Pro Asn Leu Thr Arg Thr Val Glu
         20                  25                  30

Asn Arg Gln Ile Asn Glu Glu Asp Asn Glu Ile Ser Met Leu Gln Glu
         35                  40                  45

Lys
```

```
<210> SEQ ID NO 67
<211> LENGTH: 56
<212> TYPE: PRT
<213> ORGANISM: Felis catus

<400> SEQUENCE: 67

Met Ala Leu Pro Ala Cys Phe Ser Leu Val Ile Gly Phe Ala Phe Gly
 1               5                  10                  15

Ala Phe Tyr Trp Lys Lys Lys Gln Pro Asn Leu Thr Arg Thr Val Glu
         20                  25                  30

Asn Ile Gln Ile Asn Glu Glu Asp Asn Glu Ile Ser Met Leu Gln Glu
         35                  40                  45

Lys Glu Arg Glu Phe Gln Glu Val
         50                  55
```

```
<210> SEQ ID NO 68
<211> LENGTH: 56
<212> TYPE: PRT
<213> ORGANISM: Sus scrofa

<400> SEQUENCE: 68

Val Ala Leu Pro Ala Phe Phe Ser Leu Val Ile Gly Phe Ala Phe Gly
 1               5                  10                  15

Ala Leu Tyr Trp Lys Lys Lys Gln Pro Asn Leu Thr Arg Thr Val Glu
         20                  25                  30

Asn Ile Gln Ile Asn Glu Glu Asp Asn Glu Ile Ser Met Leu Gln Glu
         35                  40                  45

Lys Glu Arg Glu Phe Gln Glu Val
         50                  55
```

```
<210> SEQ ID NO 69
<211> LENGTH: 59
<212> TYPE: PRT
<213> ORGANISM: Gallus gallus

<400> SEQUENCE: 69

Ile Ala Leu Thr Ser Leu Leu Ser Leu Leu Ile Gly Phe Ile Leu Gly
 1               5                  10                  15

Ala Ile Tyr Trp Lys Lys Thr His Pro Lys Ser Arg Pro Glu Ser Asn
         20                  25                  30

Glu Thr Ile Gln Cys His Gly Cys Gln Glu Glu Asn Glu Ile Ser Met
         35                  40                  45

Leu Gln Gln Lys Glu Lys Glu His Leu Gln Val
         50                  55
```

```
<210> SEQ ID NO 70
<211> LENGTH: 59
<212> TYPE: PRT
<213> ORGANISM: Coturnix coturnix

<400> SEQUENCE: 70

Ile Ala Leu Thr Ser Leu Leu Ser Leu Leu Ile Gly Phe Ile Leu Gly
 1               5                  10                  15
```

-continued

```
Val Ile Tyr Trp Lys Lys Thr His Pro Lys Ser Arg Pro Glu Ser Asn
                20                  25                  30

Glu Thr Thr Gln Cys His Gly Cys Gln Glu Glu Asn Glu Ile Ser Met
            35                  40                  45

Leu Gln Gln Lys Glu Lys Glu His Leu Gln Val
    50                  55
```

<210> SEQ ID NO 71
<211> LENGTH: 61
<212> TYPE: PRT
<213> ORGANISM: Ambystoma mexicanum

<400> SEQUENCE: 71

```
Val Ala Leu Ile Ser Leu Ser Ser Leu Val Leu Gly Phe Ile Ile Gly
 1               5                  10                  15

Val Val Cys Trp Lys Met Lys His Arg Glu Ser Gly Ser Gly Cys Glu
                20                  25                  30

Pro Thr Ala Pro Cys Pro Val Arg Lys Glu Ala Glu Glu Gln Ala
            35                  40                  45

Ser Met Leu Asn Gln Thr Gly Lys Ala Val His Leu Val
    50                  55                  60
```

<210> SEQ ID NO 72
<211> LENGTH: 59
<212> TYPE: PRT
<213> ORGANISM: Artificial Sequence
<220> FEATURE:
<223> OTHER INFORMATION: Consensus
<220> FEATURE:
<221> NAME/KEY: VARIANT
<222> LOCATION: 1, 4, 5, 6, 7, 10, 14, 15, 17, 18, 23, 24, 25, 26, 27,
      28, 29, 30, 31, 32, 34, 35, 37, 38, 39, 40, 41, 43, 51, 54,
      56, 57, 58
<223> OTHER INFORMATION: Xaa = Any Amino Acid

<400> SEQUENCE: 72

```
Xaa Ala Leu Xaa Xaa Xaa Xaa Ser Leu Xaa Ile Gly Phe Xaa Xaa Gly
 1               5                  10                  15

Xaa Xaa Tyr Trp Lys Lys Xaa Xaa Xaa Xaa Xaa Xaa Xaa Xaa Xaa Xaa
                20                  25                  30

Glu Xaa Xaa Gln Xaa Xaa Xaa Xaa Xaa Glu Xaa Asn Glu Ile Ser Met
            35                  40                  45

Leu Gln Xaa Lys Glu Xaa Glu Xaa Xaa Xaa Val
    50                  55
```

<210> SEQ ID NO 73
<211> LENGTH: 36
<212> TYPE: PRT
<213> ORGANISM: Mus musculus

<400> SEQUENCE: 73

```
Lys Lys Arg Gln Ser Ser Leu Thr Arg Ala Val Glu Asn Ile Gln Ile
 1               5                  10                  15

Asn Glu Glu Asp Asn Glu Ile Ser Met Leu Gln Gln Lys Glu Arg Glu
                20                  25                  30

Phe Gln Glu Val
        35
```

<210> SEQ ID NO 74
<211> LENGTH: 36
<212> TYPE: PRT
<213> ORGANISM: Mus musculus

```
<400> SEQUENCE: 74

Lys Trp Lys Trp Arg Ser Arg Asp Pro Gln Thr Leu Asp Ser Ser Val
1               5                   10                  15

Gly Arg Pro Glu Asp Ser Ser Leu Thr Gln Asp Glu Asp Arg Gln Val
            20                  25                  30

Glu Leu Pro Val
        35

<210> SEQ ID NO 75
<211> LENGTH: 4
<212> TYPE: PRT
<213> ORGANISM: Artificial Sequence
<220> FEATURE:
<223> OTHER INFORMATION: Cluster of Charged Amino-Acids

<400> SEQUENCE: 75

Asp Glu Asp Arg
1

<210> SEQ ID NO 76
<211> LENGTH: 17
<212> TYPE: PRT
<213> ORGANISM: Artificial Sequence
<220> FEATURE:
<223> OTHER INFORMATION: Junction of Tac-Tyr Chimera

<400> SEQUENCE: 76

Ser Ile Phe Thr Thr Asp Leu Gln Ala Ser Arg Ile Trp Pro Trp Leu
1               5                   10                  15

Leu

<210> SEQ ID NO 77
<211> LENGTH: 12
<212> TYPE: PRT
<213> ORGANISM: Artificial Sequence
<220> FEATURE:
<223> OTHER INFORMATION: SCF Exon 5/6 Junction

<400> SEQUENCE: 77

Ser Ser Thr Leu Gly Pro Glu Lys Asp Ser Arg Val
1               5                   10

<210> SEQ ID NO 78
<211> LENGTH: 6
<212> TYPE: PRT
<213> ORGANISM: Artificial Sequence
<220> FEATURE:
<223> OTHER INFORMATION: C-Terminus of Tac

<400> SEQUENCE: 78

Thr Ile Gln Ala Ser Ser
1               5
```